(12) United States Patent
Boga et al.

(10) Patent No.: US 7,645,583 B2
(45) Date of Patent: Jan. 12, 2010

(54) IDENTIFICATION OF COMPOUNDS FOR INHIBITING COMPLEXATION OF C-REACTIVE PROTEIN WITH FIBRONECTIN

(75) Inventors: RameshBabu Boga, Alpharetta, GA (US); Sohail Malik, Athens, GA (US); Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 607 days.

(21) Appl. No.: 11/302,994

(22) Filed: Dec. 14, 2005

(65) Prior Publication Data

US 2007/0134813 A1    Jun. 14, 2007

(51) Int. Cl.
  G01N 33/53    (2006.01)
  G01N 33/533   (2006.01)
  G01N 21/76    (2006.01)
(52) U.S. Cl. .................. 435/7.1; 435/7.93; 436/546; 436/172; 436/815
(58) Field of Classification Search ............... None
  See application file for complete search history.

(56) References Cited

U.S. PATENT DOCUMENTS

| | | | |
|---|---|---|---|
| 4,614,723 A | 9/1986 | Schmidt et al. |
| 5,075,077 A | 12/1991 | Durley, III et al. |
| 5,252,459 A | 10/1993 | Tarcha et al. |
| 5,395,754 A | 3/1995 | Lambotte et al. |
| 5,464,741 A | 11/1995 | Hendrix |
| 5,508,171 A | 4/1996 | Walling et al. |
| 5,518,883 A | 5/1996 | Soini |
| 5,534,132 A | 7/1996 | Vreeke et al. |
| 5,573,909 A | 11/1996 | Singer et al. |
| 5,585,279 A | 12/1996 | Davidson |
| 5,591,581 A | 1/1997 | Massey et al. |
| 5,637,509 A | 6/1997 | Hemmilä et al. |
| 5,670,381 A | 9/1997 | Jou et al. |
| 5,731,147 A | 3/1998 | Bard et al. |
| 5,922,537 A | 7/1999 | Ewart et al. |
| 6,004,530 A | 12/1999 | Sagner et al. |
| 6,030,840 A | 2/2000 | Mullinax et al. |
| 6,194,220 B1 | 2/2001 | Malick et al. |
| 6,241,863 B1 | 6/2001 | Monbouquette |
| 6,242,268 B1 | 6/2001 | Wieder et al. |
| 6,261,779 B1 | 7/2001 | Barbera-Guillem et al. |
| 6,270,637 B1 | 8/2001 | Crismore et al. |
| 6,281,006 B1 | 8/2001 | Heller et al. |
| 6,362,011 B1 | 3/2002 | Massey et al. |
| 6,444,423 B1 | 9/2002 | Meade et al. |
| 6,461,496 B1 | 10/2002 | Feldman et al. |
| 6,468,741 B1 | 10/2002 | Massey et al. |
| 6,582,930 B1 | 6/2003 | Ponomarev et al. |
| 6,585,939 B1 | 7/2003 | Dapprich |
| 6,613,583 B1 | 9/2003 | Richter et al. |
| 2003/0096757 A1 | 5/2003 | Quirk et al. |
| 2003/0119073 A1 | 6/2003 | Quirk et al. |
| 2003/0119202 A1 | 6/2003 | Kaylor et al. |
| 2003/0125264 A1 | 7/2003 | Malik |
| 2003/0139886 A1 | 7/2003 | Bodzin et al. |
| 2004/0043502 A1 | 3/2004 | Song et al. |
| 2004/0047827 A1 | 3/2004 | Malik |
| 2004/0116356 A1 | 6/2004 | Malik |
| 2004/0116511 A1 | 6/2004 | Malik |
| 2004/0127420 A1 | 7/2004 | Quirk |
| 2004/0127421 A1 | 7/2004 | Malik et al. |
| 2004/0259802 A1 | 12/2004 | Yang et al. |
| 2005/0239710 A1 | 10/2005 | Quirk et al. |

FOREIGN PATENT DOCUMENTS

WO    WO 03016520 A    2/2003

OTHER PUBLICATIONS

Swanson S J et al: "Binding and immunological properties of a synthetic peptide corresponding to the phosphorylcholine-binding region of C-reative protein." Molecular Immunology. Jul. 1990, vol. 27, No. 7, Jul. 1990, pp. 679-687.

International Search Report dated Nov. 28, 2006 for Int'l Application No. PCT/US2006/026454.

Article—*C-reactive Protein*, Black et al., The Journal of Biological Chemistry, vol. 279, No. 47, Nov. 19, 2004, pp. 48487-48490.

(Continued)

*Primary Examiner*—Shafiqul Haq
(74) *Attorney, Agent, or Firm*—Dority & Manning, P.A.

(57) ABSTRACT

Disclosed are screening processes for identification of compounds that may inhibit complex formation between C-reactive protein and fibronectin. Compounds identified by the disclosed methods may be utilized to inhibit the target analytes that are known to occur during skin aging as well as during the course of several diseases. Accordingly, inhibitory compounds identified by the disclosed methods may be utilized to prevent and treat damaged tissue, inflammatory conditions, cardiovascular conditions, renal conditions, periodontal conditions and obesity, among other conditions. For example, the compounds identified by the disclosed methods may be utilized to treat tissue that has suffered trauma, e.g., burns or wounds, as well as tissue that is inflamed due to any of several causes. The disclosed compounds may also be utilized to improve the accuracy of assays designed to assess CRP or Fn levels in a sample, for instance in a plasma sample, as a risk assessment tool in certain medical conditions and to discover new treatments.

17 Claims, 2 Drawing Sheets

OTHER PUBLICATIONS

Article—*C-Reactive Protein: A New Risk Assessment Tool for Cardiovascular Disease*, Michael B. Clearfield, JAOA, vol. 105, No. 9, Sep. 2005, pp. 409-416.

Article—*C-Reactive Protein, a Sensitive Marker of Inflammation, Predicts Future Risk of Coronary Heart Disease in Initially Healthy Middle-Aged Men*, Koenig et al., Circulation, vol. 99, Jan. 19, 1999, pp. 237-242.

Article—*C-reactive protein and cardiovascular disease: new insights from an old molecule*, Hirschfield et al., QJM, vol. 96, No. 11, 2003, pp. 793-807.

Article - *C-Reactive Protein and Other Markers of Inflammation in the Prediction of Cardiovascular Disease in Women*, Ridker et al., The New England Journal of Medicine, vol. 342, No. 12, Mar. 23, 2000, pp. 836-843.

Article—*C-Reactive Protein as a Cardiovascular Risk Factor—More Than an Epiphenomenon?*, Lagrand et al., Circulation, vol. 100, Jul. 6, 1999, pp. 96-102.

Article—*C-Reactive Protein in Healthy Subjects: Associations With Obesity, Insulin Resistance, and Endothelial Dysfunction—A Potential Role for Cytokines Originating from Adipose Tissue?*, Yudkin et al., Arterioscler. Thromb; Vasc. Biol., vol. 19, Apr. 1999, pp. 972-978.

Article—*Clinical Application of C-Reactive Protein for Cardiovascular Disease Detection and Prevention*, Paul M. Ridker, Circulation, vol. 107, Jan. 28, 2003, pp. 363-369..

Article—*Conformational States of Fibronectin*, Williams et al., The Journal of Biological Chemistry, vol. 257, No. 24, Dec. 25, 1982, pp. 14973-14978.

Article—*Elevated C-Reactive Protein Levels in Overweight and Obese Adults*, Visser et al., JAMA, vol. 282, No. 22, Dec. 8, 1999, pp. 2131-2135.

Article—*Endothelial dysfunction as a possible link between C-reactive protein levels and cardiovascular disease*, Cleland et al., Clinical Science, vol. 98, 2000, pp. 531-535.

Article—*Fibrinogen: biochemistry, epidemiology and determinants*, Kamath et al., QJM, vol. 96, No. 10, 2003, pp. 711-729.

Article—*Fibronectin and Wound Healing*, Journal of Cellular Biology, vol. 26, No. 2, 1984, pp. 107-116.

Article—*Interaction of Calcium-bound C-reactive Protein with Fibronectin Is Controlled by pH*, Suresh et al., The Journal of Biological Chemistry, vol. 279, No. 50, Dec. 10, 2004, pp. 52552-52557.

Article—*Primary Structure of Human Plasma Fibronectin*, Garcia-Pardo, et al., The Journal of Biological Chemistry, vol. 260, No. 18, Aug. 25, 1985, pp. 10320-10325.

Abstract of Article—*Effect of auranofin on plasma fibronectin, C reactive protein, and albumin levels in arthritic rats*, Connolly et al., Annals of the Rheumatic Diseases, vol. 47, 1988, pp. 515-521.

Abstract of Article—*Review: Biology and relevance of C-reactive protein in cardiovascular and renal disease*, Westhuyzen et al., Annals of Clinical and Laboratory Science, vol. 30, Issue 2, 2000, pp. 133-143.

Abstract of Article—*Serum C-reactive Protein and* Chlamydia trachomatis *Antibodies in Preterm Delivery*, Karinen et al., Obstetrics & Gynecology, vol. 106, 2005, pp. 73-80.

Article—*Analysis of Binding Sites in Human C-reactive Protein for FcγRI, FcγRIIA, and C1q by Site-directed Mutagenesis*, Bang et al., The Journal of Biological Chemistry, vol. 280, No. 26, Jul. 1, 2005, pp. 25095-25102.

Article—*Binding of Fibronectin by the Acute Phase Reactant C-reactive Protein*, Salonen et al., The Journal of Biological Chemistry, vol. 259, No. 3, Feb. 10, 1984, pp. 1496-1501.

Article—*Binding of Human C-Reactive Protein (CRP) to Plasma Fibronectin Occurs Via the Phosphorylcholine-Binding Site*, Tseng et al., Molecular Immunology, vol. 25, No. 8, 1988, pp. 679-686.

Article—*Probing the Phosphocholine-binding Site of Human C-reactive Protein by Site-directed Mutagenesis*, Agrawal, et al., The Journal of Biological Chemistry, vol. 267, No. 35, Dec. 15, 1992, pp. 25352-25358.

Article—*One-step all-in-one dry reagent immunoassays with fluorescent europium chelate label and time-resolved fluorometry*, Lövgren et al., Clinical Chemistry, vol. 42, No. 8, 1996, pp. 1196-1201.

Article—*A New Tetradentate β-Diketonate-Europium Chelate That Can Be Covalently Bound to Proteins for Time-Resolved Fluoroimmunoassay*, Yuan et al., Analytical Chemistry, vol. 70, No. 3, Feb. 1, 1998, pp. 596-601.

```
                        SEQUENCE LISTING

<160> NUMBER OF SEQ ID NOS: 20

<210> SEQ ID NO 1
<211> LENGTH: 8
<212> TYPE: PRT
<213> ORGANISM: Homo sapiens

<400> SEQUENCE: 1

Pro Arg Cys Gly Val Pro Asp Val
 1               5

<210> SEQ ID NO 2
<211> LENGTH: 44
<212> TYPE: PRT
<213> ORGANISM: Homo sapiens

<400> SEQUENCE: 2

Met Gln Lys Phe Phe Gly Leu Pro Gln Thr Gly Asp Leu Asp Gln Asn
 1               5                  10                  15

Thr Ile Glu Thr Met Arg Lys Pro Arg Cys Gly Asn Pro Asp Val Ala
                20                  25                  30

Asn Tyr Asn Phe Phe Pro Arg Lys Pro Lys Trp Asp
            35                  40

<210> SEQ ID NO 3
<211> LENGTH: 50
<212> TYPE: PRT
<213> ORGANISM: Homo sapiens

<400> SEQUENCE: 3

Met Gln Ser Phe Phe Gly Leu Glu Val Thr Gly Lys Leu Asp Asp Asn
 1               5                  10                  15
```

```
Thr Leu Asp Val Met Lys Lys Pro Arg Cys Gly Val Pro Asp Val Gly
            20                  25                  30

Glu Tyr Asn Val Phe Pro Arg Thr Leu Lys Trp Ser Lys Met Asn Leu
            35                  40                  45

Thr Tyr
    50

<210> SEQ ID NO 4
<211> LENGTH: 56
<212> TYPE: PRT
<213> ORGANISM: Homo sapiens

<400> SEQUENCE: 4

Met Gln Lys Phe Phe Gly Leu Pro Glu Thr Gly Lys Leu Ser Pro Arg
  1               5                  10                  15

Val Met Glu Ile Met Gln Lys Pro Arg Cys Gly Val Pro Asp Val Ala
            20                  25                  30

Glu Phe Ser Leu Met Pro Asn Ser Pro Lys Trp His Ser Arg Thr Val
            35                  40                  45

Thr Tyr Arg Ile Val Ser Tyr Thr
            50                  55

<210> SEQ ID NO 5
<211> LENGTH: 54
<212> TYPE: PRT
<213> ORGANISM: Homo sapiens

<400> SEQUENCE: 5

Met Gln Lys Phe Leu Gly Leu Glu Val Thr Gly Lys Leu Asp Ser Asp
  1               5                  10                  15

Thr Leu Glu Val Met Arg Lys Pro Arg Cys Gly Val Pro Asp Val Gly
            20                  25                  30

His Phe Arg Thr Phe Pro Gly Ile Pro Lys Trp Arg Lys Thr His Leu
            35                  40                  45

Thr Tyr Arg Ile Val Asn
            50

<210> SEQ ID NO 6
<211> LENGTH: 55
<212> TYPE: PRT
<213> ORGANISM: Homo sapiens

<400> SEQUENCE: 6

Met Gln Lys Phe Leu Gly Leu Glu Val Thr Gly Lys Leu Asp Thr Asp
  1               5                  10                  15

Thr Leu Glu Val Met Arg Lys Pro Arg Cys Gly Val Pro Asp Val Gly
            20                  25                  30

His Phe Ser Ser Phe Pro Gly Met Pro Lys Trp Arg Lys Thr His Leu
            35                  40                  45

Thr Tyr Arg Ile Val Asn Tyr
            50                  55

<210> SEQ ID NO 7
<211> LENGTH: 54
<212> TYPE: PRT
<213> ORGANISM: Homo sapiens

<400> SEQUENCE: 7

Met Gln His Phe Leu Gly Leu Lys Val Thr Gly Gln Leu Asp Thr Ser
  1               5                  10                  15
```

```
Thr Leu Glu Met Met His Ala Pro Arg Cys Gly Val Pro Asp Val His
             20                  25                  30

His Phe Arg Glu Met Pro Gly Gly Pro Val Trp Arg Lys His Tyr Ile
         35                  40                  45

Thr Tyr Arg Ile Asn Asn
     50

<210> SEQ ID NO 8
<211> LENGTH: 47
<212> TYPE: PRT
<213> ORGANISM: Homo sapiens

<400> SEQUENCE: 8

Leu Gln Lys Gln Leu Ser Leu Pro Glu Thr Gly Glu Leu Asp Ser Ala
 1               5                  10                  15

Thr Leu Lys Ala Met Arg Thr Pro Arg Cys Gly Val Pro Asp Leu Gly
             20                  25                  30

Arg Phe Gln Thr Phe Glu Gly Asp Leu Lys Trp His His His Asn
         35                  40                  45

<210> SEQ ID NO 9
<211> LENGTH: 54
<212> TYPE: PRT
<213> ORGANISM: Homo sapiens

<400> SEQUENCE: 9

Met Gln Glu Phe Phe Gly Leu Lys Val Thr Gly Lys Pro Asp Ala Glu
 1               5                  10                  15

Thr Leu Lys Val Met Lys Gln Pro Arg Cys Gly Val Pro Asp Val Ala
             20                  25                  30

Gln Phe Val Leu Thr Glu Gly Asn Pro Arg Trp Glu Gln Thr His Leu
         35                  40                  45

Thr Tyr Arg Ile Glu Asn
     50

<210> SEQ ID NO 10
<211> LENGTH: 55
<212> TYPE: PRT
<213> ORGANISM: Homo sapiens

<400> SEQUENCE: 10

Met Gln Arg Phe Phe Gly Leu Asn Val Thr Gly Lys Pro Asn Glu Glu
 1               5                  10                  15

Thr Leu Asp Met Met Lys Lys Pro Arg Cys Gly Val Pro Asp Ser Gly
             20                  25                  30

Gly Phe Met Leu Thr Pro Gly Asn Pro Lys Trp Glu Arg Thr Asn Leu
         35                  40                  45

Thr Tyr Arg Ile Arg Asn Tyr
     50                  55

<210> SEQ ID NO 11
<211> LENGTH: 19
<212> TYPE: PRT
<213> ORGANISM: Homo sapiens

<400> SEQUENCE: 11

Pro Arg Cys Gly Asn Pro Asp Val Ala Asn Tyr Asn Phe Phe Pro Arg
 1               5                  10                  15

Lys Pro Lys
```

<210> SEQ ID NO 12
<211> LENGTH: 10
<212> TYPE: PRT
<213> ORGANISM: Homo sapiens

<400> SEQUENCE: 12

```
Asn Tyr Asn Phe Phe Pro Arg Lys Pro Lys
 1               5                  10
```

<210> SEQ ID NO 13
<211> LENGTH: 660
<212> TYPE: PRT
<213> ORGANISM: Homo sapiens

<400> SEQUENCE: 13

```
Met Glu Ala Leu Met Ala Arg Gly Ala Leu Thr Gly Pro Leu Arg Ala
 1               5                  10                  15

Leu Cys Leu Leu Gly Cys Leu Leu Ser His Ala Ala Ala Ala Pro Ser
            20                  25                  30

Pro Ile Ile Lys Phe Pro Gly Asp Val Ala Pro Lys Thr Asp Lys Glu
        35                  40                  45

Leu Ala Val Gln Tyr Leu Asn Thr Phe Tyr Gly Cys Pro Lys Glu Ser
    50                  55                  60

Cys Asn Leu Phe Val Leu Lys Asp Thr Leu Lys Lys Met Gln Lys Phe
 65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
        275                 280                 285

Gln Pro Cys Lys Phe Pro Phe Arg Phe Gln Gly Thr Ser Tyr Asp Ser
    290                 295                 300

Cys Thr Thr Glu Gly Arg Thr Asp Gly Tyr Arg Trp Cys Gly Thr Thr
305                 310                 315                 320
```

```
Glu Asp Tyr Asp Arg Asp Lys Lys Tyr Gly Phe Cys Pro Glu Thr Ala
                325                 330                 335
Met Ser Thr Val Gly Gly Asn Ser Glu Gly Ala Pro Cys Val Phe Pro
            340                 345                 350
Phe Thr Phe Leu Gly Asn Lys Tyr Glu Ser Cys Thr Ser Ala Gly Arg
        355                 360                 365
Ser Asp Gly Lys Met Trp Cys Ala Thr Thr Ala Asn Tyr Asp Asp Asp
    370                 375                 380
Arg Lys Trp Gly Phe Cys Pro Asp Gln Gly Tyr Ser Leu Phe Leu Val
385                 390                 395                 400
Ala Ala His Glu Phe Gly His Ala Met Gly Leu Glu His Ser Gln Asp
            405                 410                 415
Pro Gly Ala Leu Met Ala Pro Ile Tyr Thr Tyr Thr Lys Asn Phe Arg
        420                 425                 430
Leu Ser Gln Asp Asp Ile Lys Gly Ile Gln Glu Leu Tyr Gly Ala Ser
    435                 440                 445
Pro Asp Ile Asp Leu Gly Thr Gly Pro Thr Pro Thr Leu Gly Pro Val
450                 455                 460
Thr Pro Glu Ile Cys Lys Gln Asp Ile Val Phe Asp Gly Ile Ala Gln
465                 470                 475                 480
Ile Arg Gly Glu Ile Phe Phe Phe Lys Asp Arg Phe Ile Trp Arg Thr
            485                 490                 495
Val Thr Pro Arg Asp Lys Pro Met Gly Pro Leu Leu Val Ala Thr Phe
        500                 505                 510
Trp Pro Glu Leu Pro Glu Lys Ile Asp Ala Val Tyr Glu Ala Pro Gln
    515                 520                 525
Glu Glu Lys Ala Val Phe Phe Ala Gly Asn Glu Tyr Trp Ile Tyr Ser
530                 535                 540
Ala Ser Thr Leu Glu Arg Gly Tyr Pro Lys Pro Leu Thr Ser Leu Gly
545                 550                 555                 560
Leu Pro Pro Asp Val Gln Arg Val Asp Ala Ala Phe Asn Trp Ser Lys
            565                 570                 575
Asn Lys Lys Thr Tyr Ile Phe Ala Gly Asp Lys Phe Trp Arg Tyr Asn
        580                 585                 590
Glu Val Lys Lys Lys Met Asp Pro Gly Phe Pro Lys Leu Ile Ala Asp
    595                 600                 605
Ala Trp Asn Ala Ile Pro Asp Asn Leu Asp Ala Val Val Asp Leu Gln
610                 615                 620
Gly Gly His Ser Tyr Phe Phe Lys Gly Ala Tyr Tyr Leu Lys Leu
625                 630                 635                 640
Glu Asn Gln Ser Leu Lys Ser Val Lys Phe Gly Ser Ile Lys Ser Asp
            645                 650                 655
Trp Leu Gly Cys
            660

<210> SEQ ID NO 14
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Gln or Glu
```

```
<220> FEATURE:
<221> NAME/KEY: MOD_RES
<222> LOCATION: (5)
<223> OTHER INFORMATION: Asp or Glu
<220> FEATURE:
<221> NAME/KEY: MOD_RES
<222> LOCATION: (8)
<223> OTHER INFORMATION: Gln or Ser
<220> FEATURE:
<221> NAME/KEY: MOD_RES
<222> LOCATION: (9)
<223> OTHER INFORMATION: Asn or Ala
<220> FEATURE:
<221> NAME/KEY: MOD_RES
<222> LOCATION: (11)
<223> OTHER INFORMATION: Ile or Leu
<220> FEATURE:
<221> NAME/KEY: MOD_RES
<222> LOCATION: (12)
<223> OTHER INFORMATION: Glu or Lys
<220> FEATURE:
<221> NAME/KEY: MOD_RES
<222> LOCATION: (13)
<223> OTHER INFORMATION: Thr or Ala
<220> FEATURE:
<221> NAME/KEY: MOD_RES
<222> LOCATION: (16)
<223> OTHER INFORMATION: Lys or Thr
<220> FEATURE:
<221> NAME/KEY: MOD_RES
<222> LOCATION: (17)
<223> OTHER INFORMATION: apolar amino acid
<220> FEATURE:
<221> NAME/KEY: MOD_RES
<222> LOCATION: (18)
<223> OTHER INFORMATION: basic amino acid
<220> FEATURE:
<221> NAME/KEY: MOD_RES
<222> LOCATION: (19)
<223> OTHER INFORMATION: cysteine-like amino acid
<220> FEATURE:
<221> NAME/KEY: MOD_RES
<222> LOCATION: (20)
<223> OTHER INFORMATION: apolar amino acid
<220> FEATURE:
<221> NAME/KEY: MOD_RES
<222> LOCATION: (21)
<223> OTHER INFORMATION: polar or aliphatic amino acid
<220> FEATURE:
<221> NAME/KEY: MOD_RES
<222> LOCATION: (22)
<223> OTHER INFORMATION: apolar amino acid
<220> FEATURE:
<221> NAME/KEY: MOD_RES
<222> LOCATION: (23)
<223> OTHER INFORMATION: acidic amino acid
<220> FEATURE:
<221> NAME/KEY: MOD_RES
<222> LOCATION: (24)
<223> OTHER INFORMATION: aliphatic or polar amino acid
<220> FEATURE:
<221> NAME/KEY: MOD_RES
<222> LOCATION: (25)
<223> OTHER INFORMATION: aliphatic, apolar, or basic amino acid
<220> FEATURE:
<221> NAME/KEY: MOD_RES
<222> LOCATION: (26)
<223> OTHER INFORMATION: polar, acidic, basic, or apolar amino acid
<220> FEATURE:
<221> NAME/KEY: MOD_RES
<222> LOCATION: (27)
<223> OTHER INFORMATION: polar or aromatic amino acid
<220> FEATURE:
<221> NAME/KEY: MOD_RES
<222> LOCATION: (28)
<223> OTHER INFORMATION: polar, basic, aliphatic, or apolar amino acid
<220> FEATURE:
<221> NAME/KEY: MOD_RES
<222> LOCATION: (29)
```

```
<223> OTHER INFORMATION: aromatic, aliphatic, polar or acidic amino acid
<220> FEATURE:
<221> NAME/KEY: MOD_RES
<222> LOCATION: (30)
<223> OTHER INFORMATION: aromatic, apolar, or polar amino acid
<220> FEATURE:
<221> NAME/KEY: MOD_RES
<222> LOCATION: (31)
<223> OTHER INFORMATION: apolar or acidic amino acid
<220> FEATURE:
<221> NAME/KEY: MOD_RES
<222> LOCATION: (32)
<223> OTHER INFORMATION: basic, polar, or apolar amino acid
<220> FEATURE:
<221> NAME/KEY: MOD_RES
<222> LOCATION: (33)
<223> OTHER INFORMATION: basic, polar, aliphatic, apolar, or acidic
      amino acid
<220> FEATURE:
<221> NAME/KEY: MOD_RES
<222> LOCATION: (34)
<223> OTHER INFORMATION: apolar or aliphatic amino acid
<220> FEATURE:
<221> NAME/KEY: MOD_RES
<222> LOCATION: (35)
<223> OTHER INFORMATION: basic or aliphatic amino acid

<400> SEQUENCE: 14

Pro Xaa Thr Gly Xaa Leu Asp Xaa Xaa Thr Xaa Xaa Xaa Met Arg Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa
        35

<210> SEQ ID NO 15
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Gln or Glu
<220> FEATURE:
<221> NAME/KEY: MOD_RES
<222> LOCATION: (5)
<223> OTHER INFORMATION: Asp or Glu
<220> FEATURE:
<221> NAME/KEY: MOD_RES
<222> LOCATION: (8)
<223> OTHER INFORMATION: Gln or Ser
<220> FEATURE:
<221> NAME/KEY: MOD_RES
<222> LOCATION: (9)
<223> OTHER INFORMATION: Asn or Ala
<220> FEATURE:
<221> NAME/KEY: MOD_RES
<222> LOCATION: (11)
<223> OTHER INFORMATION: Ile or Leu
<220> FEATURE:
<221> NAME/KEY: MOD_RES
<222> LOCATION: (12)
<223> OTHER INFORMATION: Glu or Lys
<220> FEATURE:
<221> NAME/KEY: MOD_RES
<222> LOCATION: (13)
<223> OTHER INFORMATION: Thr or Ala
<220> FEATURE:
<221> NAME/KEY: MOD_RES
<222> LOCATION: (16)
<223> OTHER INFORMATION: Lys or Thr
<220> FEATURE:
```

```
<221> NAME/KEY: MOD_RES
<222> LOCATION: (21)
<223> OTHER INFORMATION: Val or Asn
<220> FEATURE:
<221> NAME/KEY: MOD_RES
<222> LOCATION: (24)
<223> OTHER INFORMATION: Val or Leu
<220> FEATURE:
<221> NAME/KEY: MOD_RES
<222> LOCATION: (25)
<223> OTHER INFORMATION: Ala or Gly
<220> FEATURE:
<221> NAME/KEY: MOD_RES
<222> LOCATION: (26)
<223> OTHER INFORMATION: Asn or Arg
<220> FEATURE:
<221> NAME/KEY: MOD_RES
<222> LOCATION: (27)
<223> OTHER INFORMATION: Tyr or Phe
<220> FEATURE:
<221> NAME/KEY: MOD_RES
<222> LOCATION: (28)
<223> OTHER INFORMATION: Asn or Gln
<220> FEATURE:
<221> NAME/KEY: MOD_RES
<222> LOCATION: (29)
<223> OTHER INFORMATION: Phe or Thr
<220> FEATURE:
<221> NAME/KEY: MOD_RES
<222> LOCATION: (31)
<223> OTHER INFORMATION: Pro or Glu
<220> FEATURE:
<221> NAME/KEY: MOD_RES
<222> LOCATION: (32)
<223> OTHER INFORMATION: Arg or Gly
<220> FEATURE:
<221> NAME/KEY: MOD_RES
<222> LOCATION: (33)
<223> OTHER INFORMATION: Lys or Asp
<220> FEATURE:
<221> NAME/KEY: MOD_RES
<222> LOCATION: (34)
<223> OTHER INFORMATION: Pro or Leu

<400> SEQUENCE: 15

Pro Xaa Thr Gly Xaa Leu Asp Xaa Xaa Thr Xaa Xaa Xaa Met Arg Xaa
 1               5                  10                  15

Pro Arg Cys Gly Xaa Pro Asp Xaa Xaa Xaa Xaa Xaa Xaa Phe Xaa Xaa
                20                  25                  30

Xaa Xaa Lys
        35

<210> SEQ ID NO 16
<211> LENGTH: 9
<212> TYPE: PRT
<213> ORGANISM: Homo sapiens

<400> SEQUENCE: 16

Pro Arg Cys Gly Asn Pro Asp Val Ala
 1               5

<210> SEQ ID NO 17
<211> LENGTH: 255
<212> TYPE: PRT
<213> ORGANISM: Homo sapiens

<400> SEQUENCE: 17

His Arg Pro Arg Pro Tyr Pro Pro Asn Val Gly Gln Glu Ala Leu Ser
 1               5                  10                  15

Gln Thr Thr Ile Ser Trp Ala Pro Phe Gln Gln Thr Ser Glu Tyr Ile
                20                  25                  30
```

-continued

```
Ile Ser Cys His Pro Val Gly Thr Asp Glu Glu Pro Leu Gln Phe Arg
            35                  40                  45

Val Pro Gly Thr Ser Thr Ser Ala Thr Leu Thr Gly Leu Thr Arg Gly
 50                  55                  60

Ala Thr Tyr Asn Ile Ile Val Glu Ala Leu Lys Asp Gln Gln Arg His
 65                  70                  75                  80

Lys Val Arg Glu Val Val Thr Val Gly Asn Ser Val Asn Glu Gly
                 85                  90                  95

Leu Asn Gln Pro Thr Asp Asp Ser Cys Phe Asp Pro Tyr Thr Val Ser
                100                 105                 110

His Tyr Ala Val Gly Asp Glu Trp Glu Arg Met Ser Glu Ser Gly Phe
                115                 120                 125

Lys Leu Leu Cys Gln Cys Leu Gly Phe Gly Ser Gly His Phe Arg Cys
            130                 135                 140

Asp Ser Ser Arg Gln Cys His Asp Asn Gly Val Asn Tyr Lys Ile Gly
145                 150                 155                 160

Glu Lys Trp Asp Arg Gln Gly Glu Asn Gly Gln Met Met Ser Cys Thr
                165                 170                 175

Cys Leu Gly Met Gly Lys Gly Glu Phe Lys Cys Asp Pro His Glu Ala
                180                 185                 190

Thr Cys Tyr Asp Asp Gly Lys Thr Tyr His Val Gly Glu Gln Trp Gln
                195                 200                 205

Lys Glu Tyr Leu Gly Ala Ile Cys Ser Cys Thr Cys Phe Gly Gly Gln
            210                 215                 220

Arg Gly Trp Arg Cys Asp Asn Cys Arg Arg Pro Gly Gly Glu Pro Ser
225                 230                 235                 240

Pro Glu Gly Thr Thr Gly Gln Ser Tyr Asn Gln Tyr Ser Gln Arg
                245                 250                 255

<210> SEQ ID NO 18
<211> LENGTH: 21
<212> TYPE: PRT
<213> ORGANISM: Homo sapiens

<400> SEQUENCE: 18

Trp Glu Arg Met Ser Glu Ser Gly Phe Lys Leu Leu Cys Gln Cys Leu
  1               5                  10                  15

Gly Phe Gly Ser Gly
             20

<210> SEQ ID NO 19
<211> LENGTH: 224
<212> TYPE: PRT
<213> ORGANISM: Homo sapiens

<400> SEQUENCE: 19

Met Glu Lys Leu Leu Cys Phe Leu Val Leu Thr Ser Leu Ser His Ala
  1               5                  10                  15

Phe Gly Gln Thr Asp Met Ser Arg Lys Ala Phe Val Phe Pro Lys Glu
                 20                  25                  30

Ser Asp Thr Ser Tyr Val Ser Leu Lys Ala Pro Leu Thr Lys Pro Leu
             35                  40                  45

Lys Ala Phe Thr Val Cys Leu His Phe Tyr Thr Glu Leu Ser Ser Thr
         50                  55                  60

Arg Gly Thr Val Phe Ser Arg Met Pro Pro Arg Asp Lys Thr Met Arg
 65                  70                  75                  80
```

```
Phe Phe Ile Phe Trp Ser Lys Asp Ile Gly Tyr Ser Phe Thr Val Gly
                85              90              95

Gly Ser Glu Ile Leu Phe Glu Val Pro Glu Val Thr Val Ala Pro Val
            100             105             110

His Ile Cys Thr Ser Trp Glu Ser Ala Ser Gly Ile Val Glu Phe Trp
            115             120             125

Val Asp Gly Lys Pro Arg Val Arg Lys Ser Leu Lys Lys Gly Tyr Thr
        130             135             140

Val Gly Ala Glu Ala Ser Ile Ile Leu Gly Gln Glu Gln Asp Ser Phe
145             150             155             160

Gly Gly Asn Phe Glu Gly Ser Gln Ser Leu Val Gly Asp Ile Gly Asn
            165             170             175

Val Asn Met Trp Asp Phe Val Leu Ser Pro Asp Glu Ile Asn Thr Ile
            180             185             190

Tyr Leu Gly Gly Pro Phe Ser Pro Asn Val Leu Asn Trp Arg Ala Leu
            195             200             205

Lys Tyr Glu Val Gln Gly Glu Val Phe Thr Lys Pro Gln Leu Trp Pro
        210             215             220

<210> SEQ ID NO 20
<211> LENGTH: 21
<212> TYPE: PRT
<213> ORGANISM: Homo sapiens

<400> SEQUENCE: 20

Pro Lys Glu Ser Asp Thr Ser Tyr Val Ser Leu Lys Ala Pro Leu Thr
  1               5                  10                  15

Lys Pro Leu Lys Ala
            20
```

IDENTIFICATION OF COMPOUNDS FOR INHIBITING COMPLEXATION OF C-REACTIVE PROTEIN WITH FIBRONECTIN

BACKGROUND OF THE INVENTION

One of the characteristics of a disease state is the imbalance of chemicals that may develop as compared to the normal, healthy levels of the materials. For example, many abnormal conditions such as infection, inflammation and trauma are characterized by an elevation in C-reactive protein plasma levels and a decrease in fibronectin (Fn) plasma levels. C-reactive protein (CRP) is a member of the pentraxin family of proteins and is formed of five identical subunits that are noncovalently linked to one another. It is one of the many acute-phase proteins, increasing by roughly 1,000-fold in response to the onset of trauma. Fn, on the other hand, is a negative acute phase reactant, and levels of the soluble form of the protein as is found in plasma as well as other bodily fluids decrease rapidly following tissue damage or destruction. Fn is formed of a single polypeptide chain that includes three different types of repeating modules and is involved in many cellular processes including tissue repair, embryogenesis, blood clotting, and cell migration/adhesion.

Another characteristic of an abnormal physical condition is an alteration in how the chemicals of the body interact with one another. For example, at normal physiological condition CRP and Fn do not interact. It has been discovered, however, that binding of Fn by CRP increases greatly at mildly acidic conditions, which is a characteristic feature of the inflammatory locus.

It is believed that if the chemical state at a site of abnormal physical condition may be altered to more closely resemble that of the normal state, healing and recovery may better proceed. For example, if the chemistry that characterizes a disease site, e.g., a chronic wound or an inflammation site, may be brought closer in line with the healthy chemistry, improvement and healing at the disease site may rapidly follow.

Accordingly, what is needed in the art are methods for the identification of compounds that may then be utilized to alter the chemistry at a site of disease or damage to more closely resemble the healthy, desired chemistry and thus promote a return to health at the site. In addition, what is needed in the art are methods and compounds for examining the chemistry of disease states, so as to improve understanding of both the disease state itself as well as the activity of active compounds upon development and recovery of the disease state.

SUMMARY OF THE INVENTION

In one embodiment, the present invention is directed to a method for identifying a compound that inhibits the complexation of C-reactive protein with fibronectin. For instance, the method includes contacting a first polypeptide with a test compound, contacting the first polypeptide with a second polypeptide, and determining whether complexation of the first polypeptide with the second polypeptide is decreased in the presence of the test compound. More specifically, the first polypeptide includes at least a fragment of a C-reactive protein, and in particular the fibronectin binding site of the C-reactive protein, and the second polypeptide includes at least a fragment of a fibronectin protein, and in particular the C-reactive protein binding site of the fibronectin. According to the method, a decrease in complexation of the two polypeptides is an indication that the test compound inhibits the complexation of C-reactive protein to fibronectin.

In another embodiment, the invention is directed to a method for inhibiting the complexation of C-reactive protein with fibronectin. For example, the method may include exposing C-reactive protein and fibronectin to an effective amount of an inhibitor identified according to the disclosed methods.

The invention is also directed to a method for treating damaged or inflamed tissue. For example the method may include applying a composition to damaged or inflamed tissue that includes both C-reactive protein and fibronectin. In particular, the composition may include an effective amount of an inhibitor identified according to the disclosed methods. For example, the composition may include the inhibitor in an amount between about 0.001% and about 90% by weight of the composition.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, in which.

Figure 1:
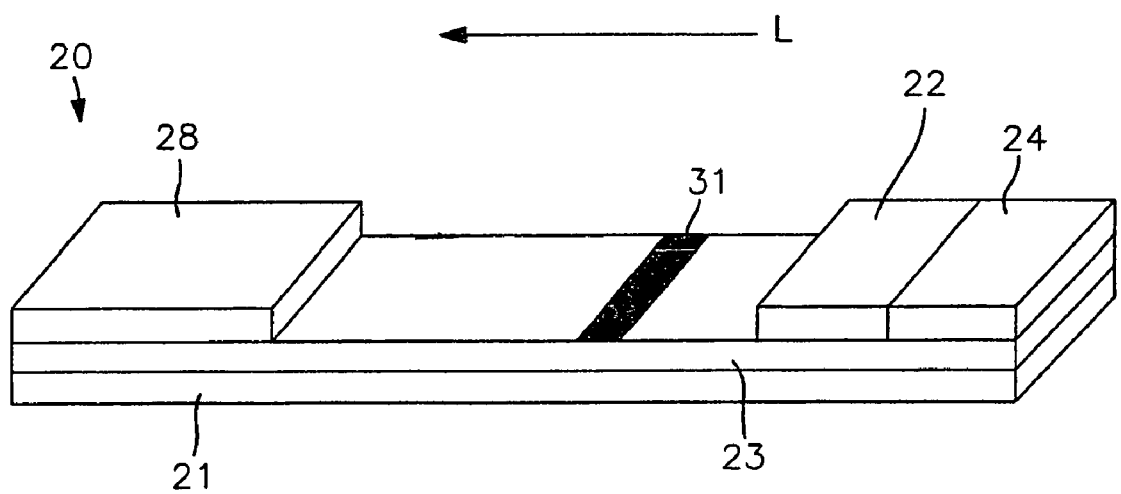
FIG. 1 is a perspective view of one embodiment of a lateral flow device suitable for use in the screening methods of the present invention.

Repeat use of reference characters in the present specification and drawings is intended to represent same or analogous features or elements of the invention.

SEQUENCE LISTINGS

SEQ ID NO.:1-SEQ ID NO.: 12 depict exemplary polypeptides of the present invention capable of inhibiting the complexation of C-reactive protein with fibronectin.

SEQ ID NO.: 13 depicts the MMP-2 sequence as herein described.

SEQ ID NO.: 14 depicts an exemplary polypeptide of the present invention capable of inhibiting the complexation of C-reactive protein with fibronectin.

SEQ ID NO.: 15 depicts another exemplary polypeptide of the present invention capable of inhibiting the complexation of C-reactive protein with fibronectin.

SEQ ID NO.: 16 depicts a 9 mer segment of SEQ ID NO.:11, specifically, the first nine amino acids of SEQ ID NO.:11.

SEQ ID NO.: 17 depicts the 31 kDa domain of human plasma fibronectin (255 residues).

SEQ ID NO.: 18 depicts the fragment of SEQ ID NO.:17 from amino acid residue 120 to amino acid residue 140.

SEQ ID NO.:19 depicts human C-reactive protein.

SEQ ID NO.: 20 depicts the fragment of SEQ ID NO.:19 from amino acid residue 30 to amino acid residue 50.

DETAILED DESCRIPTION OF REPRESENTATIVE EMBODIMENTS

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

Definitions

The definitions of the classes of amino acids as used herein are as follows:

"Hydrophobic amino acid" refers to an amino acid having a side chain that is uncharged at physiological pH and that is repelled by aqueous solution. Examples of genetically encoded hydrophobic amino acids include isoleucine, leucine and valine. An example of a non-genetically encoded hydrophobic amino acid is t-butylalanine.

"Aromatic amino acid" refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, pyridylalanine, 3-benzothienyl alanine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar amino acid" refers to a hydrophobic amino acid having a side chain that is generally uncharged at physiological pH and that is not polar. Examples of genetically encoded apolar amino acids include glycine, proline and methionine. An example of a non-encoded apolar amino acid is D-cyclohexylalanine.

"Aliphatic amino acid" refers to an apolar amino acid having a saturated or unsaturated straight chain, branched or cyclic hydrocarbon side chain. Examples of genetically encoded aliphatic amino acids include alanine, valine, leucine, and isoleucine. Examples of non-encoded aliphatic amino acids include, for example, t-butylalanine, N-methylisoleucine, norleucine, N-methylvaline, cyclohexylalanine, β-alanine, N-methylglycine, or α-aminoisobutyric acid.

"Hydrophilic amino acid" refers to an amino acid having a side chain that is attracted by aqueous solution. Examples of genetically encoded hydrophilic amino acids include serine and lysine. Examples of non-encoded hydrophilic amino acids include citrulline and homocysteine.

"Acidic amino acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic amino acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include omithine, canavanine, 2,3-diaminopropionic acid, 2,4-diaminobutyric acid, ρ-aminophenylalanine, and homoarginine.

"Polar amino acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine, serine and glutamine. Examples of non-genetically encoded polar amino acids include citrulline, threonine, tyrosine, or homoserine, N-acetyl lysine and methionine sulfoxide.

"Cysteine-like amino acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine, or β-methyl cysteine.

"Polypeptide" refers to a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations, and so forth.

"Protein" refers to any molecular chain of amino acids that is capable of interacting structurally, enzymatically or otherwise with other proteins, polypeptides or any other organic or inorganic molecule.

"Fragment" refers to an amino acid sequence of a protein or polypeptide that is shorter than the entire protein or polypeptide, but contains at least about 25 consecutive amino acids of the full protein or polypeptide.

DETAILED DESCRIPTION

In one embodiment, the present invention is directed to methods for identifying compounds that may inhibit the complexation of C-reactive protein (CRP) with Fibronectin (Fn). In other embodiments, the present invention is directed to compounds identified by the disclosed methods as well as to applications for the identified compounds. For example, compounds identified according to the disclosed methods may be beneficially utilized to inhibit the complexation of CRP with Fn to promote healing at sites of disease or damage characterized by the complexation of these materials. In another embodiment, the identified compounds may be utilized to test and further examine a variety of biologically active materials in order to determine activity of such materials during disease states such as chronic wounds, cardiovascular disease, and inflammatory disease. In another embodiment, the identified compounds may be utilized to provide improved screening methods for active biological compounds.

At normal physiological conditions, CRP is known to circulate in the blood bound to $Ca^{2+}$ and does not bind Fn. During certain disease states, however, CRP/Fn binding does occur, resulting in the formation of a CRP/Fn complex. It is presently believed that CRP/Fn interaction at healthy pH (i.e., pH near 7.0) is inhibited by the calcium ion binding, but that this effect does not extend to lower pH. Such low pH states have been found in vivo for instance at sites of infection, inflammation, trauma, and necrosis, as well as at tumors. In fact, the relatively low pH of many disease sites has been implicated as a mechanism leading to the formation of the CRP/Fn complex (see, for example, Suresh, et al., *J. Biol. Chem.*, 279:50, pp. 52552-52557 (2004)). Accordingly, in one embodiment, compounds identified according to the disclosed screening methods may be utilized to inhibit complexation of CRP with Fn at low pH conditions, such as those found in vivo in certain disease states, in order to promote healing and/or development of a desired chemistry at the site. In another embodiment, compounds identified according to the disclosed methods may be utilized to inhibit formation of the CRP/Fn complex independent of pH.

While not wishing to be bound by any particular theory, there are several possible mechanisms through which inhibitory compounds identified according to the disclosed methods may block the formation of a CRP/Fn complex. For example, the inhibitory compounds may bind CRP at the calcium binding site, possibly through displacement of the calcium ion. In another possibility, the inhibitory compounds may bind CRP near the calcium binding site, and thus block $Ca^{2+}$ binding or otherwise interfere with the $Ca^{2+}$ interaction with CRP. Such interference could be stearic, chemical, or electrical in nature. The inhibitory compounds may also bind to calcium as a ligand (for instance through displacement of a water ligand), and thus prevent binding of the calcium ion. Possibly, the binding of the inhibitory compounds to the CRP may cause a structural change in the protein conformation, and thus prevent CRP/Fn complexation. The inhibitory compounds may interact with amino acids critical to the formation of the CRP/Fn complex, and these binding interactions may take precedence over the calcium role. Inhibitory compounds such as those specifically disclosed herein as well as those that may be identified according to the disclosed methods may utilize these or any other mechanisms, known or unknown, in preventing formation of the CRP/Fn complex.

Identification Methods

In general, the identification methods of the present invention may utilize a screening method and device for examination of a test sample containing a compound of interest in order to determine the effect of the test compound on CRP/Fn complex formation. The screening devices employed in the present invention may perform any type of screening process as is known in the art, including homogeneous and heterogeneous screening processes. A homogeneous screening process is a process in which uncomplexed labeled species are not separated from complexed labeled species. A heterogeneous screening process is a process in which uncomplexed labeled species are separated from complexed labeled species. Separation may be carried out by physical separation, e.g., by transferring one of the species to another reaction vessel, filtration, centrifugation, chromatography, solid phase capture, magnetic separation, and so forth, and may include one or more washing steps. The separation may also be non-physical in that no transfer of one or both of the species is conducted, but the species are separated from one another in situ.

The amino acid notations used herein for the twenty genetically encoded L-amino acids and common non-encoded amino acids are shown in Table 1.

TABLE 1

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |

TABLE 1-continued

| Amino Acid | One-Letter Symbol | Common Abbreviation |
|---|---|---|
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3Diaminopropionic acid | | Dpr |
| α-Aminoisobutyric acid | | Aib |
| N-Methyglycine (sarcosine) | | MeGly |
| Ornithine | | Orn |
| Canavanine | | Can |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylananine | | |
| 3-Benzothienyl alanine | | |
| 4-Chlorophenylatanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-Tic isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| ρ-Aminophenylalanine | | Phe(pNH$_2$) |
| N-methylvaline | | MeVal |
| Homocysteine | | hCys |
| Homoserine | | hSer |
| ε-Amino hexanoic acid | | Aha |
| δ-Amino valerie acid | | Ava |
| 2,3-Diaminobutyric acid | | Dab |

Polypeptides that are encompassed within the scope of the invention may have one or more amino acids substituted with an amino acid of similar chemical and/or physical properties, so long as these variant or derivative polypeptides retain the ability to function as herein described. Amino acid residues of the isolated polypeptides may be genetically encoded L-amino acids, naturally occurring non-genetically encoded L-amino acids, synthetic L-amino acids or D-enantiomers of any of the above.

Amino acids that are substitutable for each other generally reside within similar classes or subclasses. As known to one of skill in the art, amino acids may be placed into three main classes: hydrophilic amino acids, hydrophobic amino acids and cysteine-like amino acids, depending primarily on the characteristics of the amino acid side chain. These main classes may be further divided into subclasses. For instance, hydrophilic amino acids include amino acids having acidic, basic or polar side chains and hydrophobic amino acids include amino acids having aromatic or apolar side chains. Apolar amino acids may be further subdivided to include, among others, aliphatic amino acids.

As will be appreciated by those of skill in the art, the above classifications are not absolute. Several amino acids exhibit more than one characteristic property, and may therefore be included in more than one category. For example, tyrosine has both an aromatic ring and a polar hydroxyl group. Thus, tyrosine has dual properties and may be included in both the aromatic and polar categories. Similarly, in addition to being able to form disulfide linkages, cysteine also has apolar character. Thus, while not strictly classified as a hydrophobic or apolar amino acid, in many instances cysteine may be used to confer hydrophobicity to a polypeptide.

Certain commonly encountered amino acids that are not genetically encoded and that may be present, or substituted for an amino acid in the polypeptides and polypeptide analogues of the invention include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hcys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues that may comprise the polypeptides and polypeptide analogues described herein. Other amino acid residues that are useful for making the polypeptides and polypeptide analogues described herein may be found, e.g., in Fasman, 1989, CRC Practical Handbook of Biochemistry and Molecular Biology, CRC Press, Inc., and the references cited therein. Amino acids not specifically mentioned herein may be conveniently classified into the above-described categories on the basis of known behavior and/or their characteristic chemical and/or physical properties as compared with amino acids specifically identified.

TABLE 2

| Classification | Genetically Encoded | Genetically Non-Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$BU |
| Polar | Q, N, S, T, Y | Cit, AcLys, MSO, hSer |
| Cysteine-Like | C | Pen, hCys, β-methyl Cys |

The identification methods of the present invention incorporate CRP-based and Fn-based polypeptides in a screening process in order to identify compounds that inhibit the complexation of CRP with Fn. In one embodiment, the screening process may incorporate the entire protein, e.g., the entire CRP and/or Fn protein. This is not a requirement of the present invention, however, and in other embodiments, the screening methods may incorporate only a portion of the complete protein, but including a fragment that is involved in CRP/Fn complexation.

For instance, in one embodiment, the screening method of the present invention may utilize the 31 kDa domain of human Fn (SEQ ID NO.:17), or a functionally equivalent variant or derivative thereof (se, e.g., Garcia-Pardo, et al., 'Primary Structure of Human Plasma Fibronectin,' *The Journal of Biological Chemistry*, 260:18, pp. 10320-10325 (1985)). In other embodiments, the screening method of the present invention may utilize a fragment of this domain. For instance, most or all of the CRP binding site of Fn is localized to the 120-140 residue fragment of the Fn (e.g., SEQ ID NO.:18), which contains cell-binding and heparin-binding domains of the protein. Accordingly, in other embodiments, the screening method of the present invention may utilize a fragment of the Fn molecule comprising at least this binding portion of the entire protein, or a functionally equivalent variant or derivative thereof.

Similarly, the screening method may include the entire CRP protein, a single subunit of the protein, or a fragment or variant thereof capable of binding to Fn. For example, in one embodiment, an entire subunit of the 5-unit protein (e.g., SEQ ID NO.:19, GenBank Accession No.:CM39671) or a functional equivalent thereof may be utilized in the process. In another embodiment, however, a fragment of the CRP may be utilized, and in particular, a fragment including the Fn binding site of the protein. For example, the Fn binding site of CRP is understood to be localized within the 30-50 residue fragment of the CRP (e.g., SEQ ID NO.: 20). Accordingly, in one embodiment, the screening methods disclosed herein may utilize this fragment of the protein, or a functionally equivalent variant or derivative thereof.

In one preferred embodiment, the screening method of the present invention may be carried out with a lateral flow screening device.

Referring now to FIG. 1, one embodiment of a lateral flow screening device 20 that may be utilized for the disclosed identification process will now be described in more detail. As shown, the device 20 contains a fluidic medium 23 that is optionally supported by a rigid material 21. The fluidic medium 23 may include, for example, one or more porous membranes, one or more fluidic channels, or any other device or construct suitable for use as a fluidic medium as will be recognized by one of skill in the art.

In general, the fluidic medium 23 may be made from any of a variety of materials through or over which the test sample is capable of passing. For example, the materials used to form the fluidic medium 23 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, MgSO$_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the fluidic medium 23 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the fluidic medium 23 may generally vary as is readily recognized by those skilled in the art. For instance, a porous membrane strip may have a length of from about 10 to about 100 millimeters, in some embodiments from about 20 to about 80 millimeters, and in some embodiments, from about 40 to about 60 millimeters. The width of the membrane strip may range from about 0.5 to about 20 millimeters, in some embodiments from about 1 to about 15 millimeters, and in some embodiments, from about 2 to about 10 millimeters. In one embodiment, the thickness of the membrane strip may be small enough to allow transmission-based detection. For example, the membrane strip may have a thickness less than about 500 micrometers, in some embodiments less than about 250 micrometers, and in some embodiments, less than about 150 micrometers.

In the illustrated embodiment, the support 21 carries the fluidic medium 23. For example, the support 21 may be positioned directly adjacent to the fluidic medium 23 as shown in FIG. 1, or one or more intervening layers may be positioned between the fluidic medium 23 and the support 21. Regardless, the support 21 may generally be formed from any material able to carry the fluidic medium 23. The support 21 may be formed from a material that is transmissive to light, such as transparent or optically diffuse (e.g., translucent) materials. Also, it is generally desired that the support 21 is liquid-impermeable so that fluid flowing through the fluidic medium 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the fluidic medium 23, the support 21 is generally selected to have a certain minimum thickness. For example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip suitable for use as a support having a thickness of about 125 micrometers may be obtained from Millipore Corp. of Bedford, Mass. under the name "SHF180UB25."

As is well known the art, the fluidic medium 23 may be cast onto the support 21, wherein the resulting laminate may be die-cut to the desired size and shape. Alternatively, the fluidic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

The device 20 may also contain an absorbent pad 28. The absorbent pad 28 generally receives fluid that has migrated through the entire fluidic medium 23. As is well known in the art, the absorbent pad 28 may assist in promoting capillary action and fluid flow through the fluidic medium 23.

To initiate the examination of a compound within a test sample, a user may directly apply the test sample to a portion of the fluidic medium 23 through which it may then travel in the direction illustrated by arrow "L" in FIG. 1. Alternatively, the test sample may first be applied to a sample pad 24 that is in fluid communication with the fluidic medium 23. Some suitable materials that may be used to form the sample pad 24 include, but are not limited to, nitrocellulose, cellulose, porous polyethylene pads, and glass fiber filter paper.

In the illustrated embodiment, the test sample travels from the sample pad 24 to a conjugate pad 22 that is placed in communication with one end of the sample pad 24. The conjugate pad 22 is formed from a material through which the test sample is capable of passing. For example, in one embodiment, the conjugate pad 22 is formed from glass fibers. Although only one conjugate pad 22 is shown, it should be understood that multiple conjugate pads may also be used in the process. In one particular embodiment of the present invention, detection probes (not shown) may be applied to the conjugate pad 22. After application, the probes are then dried to inhibit migration therefrom. The conjugate pad 22 provides a matrix for the deposition of the probes so that they are free to migrate when rehydrated. More specifically, when a liquid test sample contacts the probes, they are rehydrated and become re-suspended and/or re-solubilized. Of course, it should be understood that the probes may be applied to various other locations of the device 20 as well, such as directly to the fluidic medium 23, so long as they are capable of being rehydrated by the test sample upon contact therewith.

To facilitate the examination of the effect of the compound of interest on the formation of the CRP/Fn complex, a detectable substance may be pre-applied to the sample pad and/or conjugate pad, or previously mixed with a diluent or test sample. The detectable substance may function as a detection probe that is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but are not limited to, fluorescein, europium chelates, phycobiliprotein, phycoerythrin, phycocyanin, allophycocyanin, o-phthaldehyde, fluorescamine, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin; porphine; and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine]2-[3-(4-methyl-2,2'-bipyridine-4-yl)propyl]-1,3-dioxolane ruthenium (II); bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid]ruthenium (II); tris(2, 2'bipyridine)ruthenium (II); (2,2'-bipyridine)[bis-bis(1,2-diphenylphosphino)ethylene]2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, luminescent compounds may have a relatively long emission lifetime and/or may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N, N-bis(carboxymethyl)amino]methyl)-pyridine [Ref: Lovgren, T., et al.; Clin. Chem. 42,1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637, 509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al.; U.S. Pat. No. 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 100 microns, in some embodiments, from about 1 nanometer to about 10 microns, and in some embodiments, from about 10 to about 100 nanometers.

In some instances, it may be desired to modify the detection probes so that they are more readily able to detect either the complexation of the CRP to the Fn or the lack of complexation of the CRP to the Fn, as desired. For example, in one embodiment, one of the two members of the complex may be modified with the detection probes to form conjugated probes.

According to this embodiment, one of the specific binding members of the complex may be attached to the detection probes using any of a variety of well-known techniques. For instance, covalent attachment of the specific binding member to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a coupling reaction may be accomplished. A surface functional group may also be incorporated as a functionalized co-monomer as the surface of the detection probe may contain a relatively high surface concentration of polar groups. In addition, although detection probes are often functionalized after synthesis, such as with poly(thiophenol), the detection probes may be capable of direct covalent linking with the specific binding member without the need for further modification. For example, in one embodiment, the first step of conjugation is activation of carboxylic groups on the probe surface using carbodiimide. In the second step, the activated carboxylic acid groups are reacted with an amino group of the CRP or the Fn to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). Overall, this process forms a conjugated detection probe, where the specific binding member of the complex is covalently attached to the probe. Besides covalent bonding, other attachment techniques, such as physical adsorption, may also be utilized.

Another technique that may also result in greater sensitivity when used in conjunction with the present invention consists of coupling the binding member of the complex to low molecular weight haptens. The haptens may then be specifically detected by means of a second reaction. For example, it is common to use such haptens as biotin (reacting with avidin) or dinitrophenol, pyridoxal and fluorescamine (reacting with specific antihapten antibodies) in this manner.

In another embodiment, either the CRP or the Fn may be detectably labeled by coupling to a chemiluminescent compound. The presence of the chemiluminescent-tagged complex is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the binding member of the complex as further described below. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Referring again to FIG. 1, the fluidic medium 23 also defines various zones configured to perform the screening process. For instance, the fluidic medium 23 may define a detection zone 31 within which is immobilized a receptive material that can, in one embodiment, bind to the conjugated detection probes that pass through the length of the fluidic medium 23 in order to detectibly demonstrate the formation of the CRP/Fn complex. The receptive material may be for instance, a nonlabeled member of the CRP/Fn complex or a material capable of specifically binding to the formed CRP/Fn complex. The receptive material may be immobilized in the detection zone according to any suitable binding method.

For example, in one embodiment, the receptive material may be a complete protein, i.e., either complete CRP or complete Fn, or optionally may be a subunit or a fragment thereof that includes the binding site for the other member of the complex. According to this embodiment, the detection zone may serve as a complex formation site between the immobilized first binding member of the complex and second binding member of the complex. In addition, the second binding member of the complex may be conjugated to a detection probe and may contact the receptive material when in the presence of the test sample. Accordingly, when the compound of interest does not inhibit formation of the complex, the complex may form and be detected via the conjugated detectable probe.

According to another embodiment, the receptive material may be a secondary material that may specifically and detectibly bind to the labeled complex. For example, the receptive material may be a polyclonal or monoclonal antibody specific for the non-labeled member of the complex. Upon reaching the detection zone 31, the CRP/Fn complex may bind to the receptive material and be detected via the detectable label conjugated to the labeled member of the complex. Optionally, the first, non-labeled binding member of the complex may contact the detection zone and bind to the receptive material prior to contact with the test compound and the detectably labeled binding member of the complex.

The detection zone 31 may provide any number of distinct detection regions so that a user may better determine the effect of a compound of interest on complexation of CRP with Fn. Each region may contain the same receptive materials, or may contain different receptive materials. For example, the zones may include two or more distinct regions (e.g., lines, dots, etc.). The regions may be disposed in the form of lines in a direction that is substantially perpendicular to the flow of the test sample through the device 20. Likewise, in some embodiments, the regions may be disposed in the form of lines in a direction that is substantially parallel to the flow of the test sample through the device 20.

Qualitative, semi-quantitative, and quantitative results may be obtained in accordance with the present invention. For example, when it is desired to semi-quantitatively or quantitatively detect the complexation of CRP with Fn at the detection zone, the intensity of any signals produced at the detection zone 31 may be measured with an optical reader. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the intensity of a fluorescence signal. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to signal intensity.

Detection and calibration may be performed automatically and/or manually in accordance with the present invention. For example, a microprocessor may optionally be employed to convert signal intensities from a detector to a result that quantitatively or semi-quantitatively indicates the concentration of the formed complex in the sample. The microprocessor may include memory capability to allow the user to recall the last several results. Those skilled in the art will appreciate that any suitable computer-readable memory devices, such as RAM, ROM, EPROM, EEPROM, flash memory cards, digital video disks, Bernoulli cartridges, and so forth, may be used. If desired, the results may be conveyed to a user using a liquid crystal (LCD) or LED display.

Although various embodiments of device configurations have been described above, it should be understood, that a device of the present invention may generally have any configuration desired, and need not contain all of the components described above. Various other device configurations, for instance, are described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes. In particular, it should be understood that any known device may be utilized that is capable of determining either the formation or the lack of formation of a CRP/Fn complex in the presence of a compound of interest in accordance with the present invention. For example, electrochemical affinity devices may also be utilized that detect an electrochemical reaction between a CRP/Fn complex and a capture ligand on an electrode strip. For example, various electrochemical assays and devices are described in U.S. Pat. No. 5,508,171 to Walling, et al.; U.S. Pat. No. 5,534,132 to Vreeke, et al.; U.S. Pat. No. 6,241,863 to Monbouquette; U.S. Pat. No. 6,270,637 to Crismore, et al.; U.S. Pat. No. 6,281,006 to Heller, et al.; and U.S. Pat. No. 6,461,496 to Feldman, et al., which are incorporated herein in their entirety by reference thereto for all purposes.

Inhibitors

In one embodiment, inhibitory compounds that may be identified according to the presently disclosed processes may be polypeptides. For instance, polypeptides that have been previously described as anti-angiogenic compositions for inhibiting matrix metalloproteinases (MMPS) as well as for diminishing the expression of vascular endothelial growth factor (see U.S. Pat. No. 6,906,036, U.S. Patent Application Publication No. 2003/0096757, U.S. Patent Application Publication No. 2004/0127420, and U.S. Patent Application Publication No. 2005/0239710, all of which are incorporated herein in their entirety by reference) have been examined according to the above described methods and found to be inhibitors of CRP/Fn complexation.

For example, inhibitory polypeptides of the present invention may have amino acid sequences identical or related to the linking region spanning the two globular domains of MMPs. In one embodiment, polypeptides with sequences from a proenzyme leader region of an MMP are encompassed by the invention. Variant polypeptides that have one or more amino acids substituted for the amino acids that are naturally present in the specific MMP are also encompassed by the present invention. Mixtures of inhibitory polypeptides with different sequences are also contemplated.

Several types of MMPs and their sequences are known to those of skill in the art. For example, in one embodiment, inhibitor polypeptides of the present invention may have amino acid sequences drawn from any region ranging from about position 70 to about position 120 of the MMP-2 sequence (SEQ ID NO: 13), or analogous regions of other MMPs. In another embodiment, the inhibitor polypeptides of the invention may have amino acid sequences ranging from about position 77 to about position 110 of SEQ ID NO:13, or analogous regions of other MMPs. Specific examples of inhibitor polypeptides of the invention include those that contain amino acid sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID:9, SEQ ID NO:10, SEQ ID NO:11, and SEQ ID NO:12. In addition, polypeptide variants and derivatives of the polypeptides having any of SEQ ID NO:1-12 may also be useful as CRP/Fn complex inhibitors. Such polypeptide variants and derivatives may have one or more amino acid substitutions, deletions, insertions or other modifications such as those described above in reference to the CRP and Fn-based polypeptides, so long as the polypeptide variant or derivative may function as herein described.

The size of the inhibitory polypeptide compounds of the invention may vary. For example, in one embodiment, polypeptides of about eight to nine amino acids are encompassed by the disclosed invention. In other embodiments, however, the polypeptides of the invention may be longer or shorter, for example, polypeptides of the invention may be longer than about ten amino acids or even longer than about fifteen amino acids in other embodiments.

There is no particular upper limit on the size of the polypeptide inhibitory compounds. As it may be more economically feasible to make shorter polypeptides than longer polypeptides, shorter polypeptides are preferred in certain embodiments of the invention. Accordingly, in one embodiment, the polypeptides of the invention may be shorter in length than about one hundred amino acids. In other embodiments, the polypeptide compounds may be shorter than about fifty amino acids, shorter than about thirty amino acids, or shorter than about twenty five amino acids. In some embodiments, the polypeptides are shorter than about twenty three amino acids.

In one embodiment, the inhibitor compounds of the present invention may be polypeptides of either of the following formulas:

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11}\text{-}Xaa_{12}\text{-}Xaa_{13}\text{-}Xaa_{14}\text{-}Xaa_{15}\text{-}Xaa_{16}\text{-}Xaa_{17}\text{-}Xaa_{18}\text{-}Xaa_{19} \quad (I)$$

$$Xaa_{10}\text{-}Xaa_{11}\text{-}Xaa_{12}\text{-}Xaa_{13}\text{-}Xaa_{14}\text{-}Xaa_{15}\text{-}Xaa_{16}\text{-}Xaa_{17}\text{-}Xaa_{18}\text{-}Xaa_{19} \quad (II)$$

wherein $Xaa_1$, $Xaa_4$ and $Xaa_6$ are separately each a polar amino acids, for example, methionine, glycine or proline;

$Xaa_2$ is a basic amino acid, for example, histidine, lysine, arginine, 2,3-diaminopropionic acid, ornithine, homoarginine, ρ-aminophenylalanine, and 2,4-diaminobutyric acid;

$Xaa_3$ is a cysteine-like amino acid, for example, cysteine, homocysteine, penicillamine, or β-methyl cysteine;

$Xaa_5$ is a polar or aliphatic amino acid, for example, a polar amino such as asparagine, glutamine, serine, threonine, tyrosine, citrulline, N-acetyl lysine, methionine sulfoxide, or homoserine, or an aliphatic amino acid such as alanine, valine, leucine, isoleucine, t-butylalanine, t-butylglycine, N-methylisoleucine, norleucine, N-methylvaline, cyclohexylalanine, β,-alanine, N-methylglycine, or α-aminoisobutyric acid;

$Xaa_7$ is an acidic amino acid, for example, aspartic acid or glutamic acid;

$Xaa_8$ is an aliphatic or polar amino acid, for example an aliphatic amino acid such as alanine, valine, leucine, isoleucine, t-butylalanine, t-butylglycine, methylisoleucine, norleucine, N-methylvaline, cyclohexylalanine, β-alanine, N-methylglycine, or α-aminoisobutyric acid, or a polar amino acid such as asparagine, glutamine, serine, threonine, tyrosine, citrulline, N-acetyl lysine, methionine sulfoxide, or homoserine;

$Xaa_9$ is an aliphatic, a polar or basic amino acid, for example, an aliphatic amino acid such as alanine, valine, leucine, isoleucine, t-butylalanine, t-butylglycine, N-methylisoleucine, norleucine, N-methylvaline, cyclohexylalanine, β-alanine, N-methylglycine, or α-aminoisobutyric acid, an apolar amino acid such as methionine, glycine or proline, or a basic amino acid such as histidine, lysine, arginine, 2,3-diaminopropionic acid, ornithine, homoarginine, ρ-amino-phenylalanine, and 2,4-diaminobutyric acid;

$Xaa_{10}$ is a polar, acidic, basic or apolar amino acid, for example, a polar amino acid such as asparagine, glutamine, serine, threonine, tyrosine, citrulline, N-acetyl lysine, methionine sulfoxide, or homoserine, an acidic amino acid such as aspartic acid or glutamic acid, a basic amino acid such as histidine, lysine, arginine, 2,3-diaminopropionic acid, ornithine, homoarginine, ρ-amino-phenylalanine, and 2,4-diaminobutyric acid, or an apolar amino acid such as methionine, glycine or proline;

$Xaa_{11}$ is a polar or aromatic amino acid, for example, a polar amino acid such as asparagine, glutamine, serine, threonine, tyrosine, citrulline, N-acetyl lysine, methionine sulfoxide, or homoserine, or an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine;

$Xaa_{12}$ is a polar, basic, aliphatic or apolar amino acid, for example, a polar amino acid such asparagine, glutamine, serine, threonine, tyrosine, citrulline, N-acetyl lysine, methionine sulfoxide, or homoserine, or a basic amino acid such as histidine, lysine, arginine, 2,3-diaminopropionic acid, ornithine, homoarginine, .rho.-amino-phenylalanine, and 2,4-diaminobutyric acid, or an aliphatic amino acid such as alanine, valine, leucine, isoleucine, t-butylalanine, t-butylglycine, N-methylisoleucine, norleucine, N-methylvaline, cyclohexylalanine, β-alanine, N-methylglycine, or α-aminoisobutyric acid, or an apolar amino acid such as methionine, glycine or proline;

$Xaa_{13}$ is an aromatic, aliphatic, polar or acidic amino acid, for example, an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine, or an aliphatic amino acid such as alanine, valine, leucine, isoleucine, t-butylalanine, t-butylglycine, N-methylisoleucine, norleucine, N-methylvaline, cyclohexylalanine, β-alanine, N-methylglycine, or α-aminoisobutyric acid, or a polar amino acid such as asparagine, glutamine, serine, threonine, tyrosine, citrulline, N-acetyl lysine, methionine sulfoxide, or homoserine, or an acidic amino acid such as aspartic acid or glutamic acid;

$Xaa_{14}$ is an aromatic, apolar or polar amino acid, for example, an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine, or an apolar amino acid such as methionine, glycine or proline, or a polar amino acid such as asparagine, glutamine, serine, threonine, tyrosine, citrulline, N-acetyl lysine, methionine sulfoxide, or homoserine;

$Xaa_{15}$ is an apolar or acidic amino acid, for example, an apolar amino acid such as methionine, glycine or proline, or an acidic amino acid such as aspartic acid or glutamic acid;

$Xaa_{16}$ is a basic, a polar or an apolar amino acid, for example, a basic amino acid such as histidine, lysine, arginine, 2,3-diaminopropionic acid, ornithine, homoarginine, ρ-amino-phenylalanine, and 2,4-diaminobutyric acid; or a polar amino acid such as asparagine, glutamine, serine, threonine, tyrosine, citrulline, N-acetyl lysine, methionine sulfoxide, or homoserine, or an apolar amino acid such as methionine, glycine or proline;

$Xaa_{17}$ is a basic, a polar, an aliphatic, an apolar or an acidic amino acid, for example, a basic amino acid such as histidine, lysine, arginine, 2,3-diaminopropionic acid, ornithine, homoarginine, ρ-amino-phenylalanine, and 2,4-diaminobutyric acid, or a polar amino acid such as asparagine, glutamine, serine, threonine, tyrosine, citrulline, N-acetyl lysine, methionine sulfoxide, or homoserine, or an aliphatic amino acid such as alanine, valine, leucine, isoleucine, t-butylalanine, t-butylglycine, N-methylisoleucine, norleucine, N-methylvaline, cyclohexylalanine, β-alanine, N-methylglycine, or α-aminoisobutyric acid, or an apolar amino acid such as methionine, glycine or proline, an acidic amino acid such as aspartic acid or glutamic acid;

$Xaa_{18}$ is an apolar or an aliphatic amino acid, for example, an apolar amino acid such as methionine, glycine or proline, or an aliphatic amino acid such as alanine, valine, leucine, isoleucine, t-butylalanine, t-butylglycine, N-methylisoleucine, norleucine, N-methylvaline, cyclohexylalanine, β-alanine, N-methylglycine, or α-aminoisobutyric acid; and $Xaa_{19}$ is a basic or an aliphatic amino acid, for example, a basic amino acid such as histidine, lysine, arginine, 2,3-diaminopropionic acid, ornithine, homoarginine, ρ-amino-phenylalanine, and 2,4-diaminobutyric acid, or an aliphatic amino acid such as alanine, valine, leucine, isoleucine, t-butylalanine, t-butylglycine, N-methylisoleucine, norleucine, N-methylvaline, cyclohexylalanine, β-alanine, N-methylglycine, or α-aminoisobutyric acid.

In one embodiment:
$Xaa_1$ is proline;
$Xaa_2$ is arginine;
$Xaa_3$ is cysteine;
$Xaa_4$ is glycine;
$Xaa_5$ is valine or asparagine;
$Xaa_6$ is proline;
$Xaa_7$ is aspartic acid;
$Xaa_8$ is valine, leucine, or serine;
$Xaa_9$ is alanine, histidine, or glycine;
$Xaa_{10}$ is asparagine, aspartic acid, histidine, arginine, glutamine, or glycine;
$Xaa_{11}$ is tyrosine or phenylalanine;
$Xaa_{12}$ is asparagine, serine, arginine, glutamine, valine, or methionine;
$Xaa_{13}$ is phenylalanine, valine, leucine, threonine, serine, or glutamic acid;
$Xaa_{14}$ is phenylalanine, methionine, or threonine;
$Xaa_{15}$ is proline or glutamic acid;
$Xaa_{16}$ is arginine, asparagine, or glycine;
$Xaa_{17}$ is lysine, threonine, serine, isoleucine, methionine, glycine, aspartic acid, or asparagine;
$Xaa_{18}$ is proline or leucine; and
$Xaa_{19}$ is lysine, valine, or arginine.

In another embodiment, a polypeptide of the invention may have the general formula:

$$Xaa_a\text{-}Xaa_b\text{-}Xaa_c\text{-}Xaa_d\text{-}Xaa_e\text{-}Xaa_f\text{-}Xaa_g\text{-}Xaa_h\text{-} \quad \text{(III)}$$
$$Xaa_i\text{-}Xaa_j\text{-}Xaa_k\text{-}Xaa_l\text{-}Xaa_m\text{-}Xaa_n\text{-}Xaa_o\text{-}Xaa_p\text{-}$$
$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}$$
$$Xaa_9\text{-}Xaa_{10}\text{-}Xaa_{11}\text{-}Xaa_{12}\text{-}Xaa_{13}\text{-}Xaa_{14}\text{-}Xaa_{15}\text{-}$$
$$Xaa_{16}\text{-}Xaa_{17}\text{-}Xaa_{18}\text{-}Xaa_{19}$$

and the polypeptide may include the following sequence (SEQ ID NO.14):
$Xaa_a$ is proline
$Xaa_b$ is glutamine or glutamic acid;
$Xaa_c$ is threonine;
$Xaa_d$ is glycine;
$Xaa_e$ is aspartic acid or glutamic acid;
$Xaa_f$ is leucine;
$Xaa_g$ is aspartic acid;
$Xaa_h$ is glutamine or serine;
$Xaa_i$ is asparagine or alanine;
$Xaa_j$ is threonine;
$Xaa_k$ is isoleucine or leucine;
$Xaa_l$ is glutamic acid or lysine;
$Xaa_m$ is threonine or alanine;
$Xaa_n$ is methionine;
$Xaa_o$ is arginine;
$Xaa_p$ is lysine or threonine;
$Xaa_1$ is an apolar amino acid;
$Xaa_2$ is a basic amino acid;
$Xaa_3$ is a cysteine-like amino acid;
$Xaa_4$ is an apolar amino acid;
$Xaa_5$ is a polar or aliphatic amino acid;
$Xaa_6$ is an apolar amino acid;
$Xaa_7$ is an acidic amino acid;
$Xaa_8$ is an aliphatic or polar amino acid;
$Xaa_9$ is an aliphatic, an apolar or a basic amino acid;
$Xaa_{10}$ is a polar, acidic, basic or apolar amino acid;
$Xaa_{11}$ is a polar or aromatic amino acid;
$Xaa_{12}$ is a polar, basic, aliphatic or apolar amino acid;
$Xaa_{13}$ is an aromatic, aliphatic, polar or acidic amino acid;
$Xaa_{14}$ is an aromatic, apolar or polar amino acid;
$Xaa_{15}$ is an apolar or acidic amino acid;
$Xaa_{16}$ is a basic, a polar or an apolar amino acid;
$Xaa_{17}$ is a basic, a polar, an aliphatic, an apolar or an acidic amino acid;
$Xaa_{18}$ is an apolar or an aliphatic amino acid;
$Xaa_{19}$ is a basic or an aliphatic amino acid.

In another embodiment, the polypeptide may include the following sequence (SEQ ID NO:15):
$Xaa_a$ is proline
$Xaa_b$ is glutamine or glutamic acid;
$Xaa_c$ is threonine;
$Xaa_d$ is glycine;
$Xaa_e$ is aspartic acid or glutamic acid;
$Xaa_f$ is leucine;
$Xaa_g$ is aspartic acid;
$Xaa_h$ is glutamine or serine;
$Xaa_i$ is asparagine or alanine;
$Xaa_j$ is threonine;
$Xaa_k$ is isoleucine or leucine;
$Xaa_l$ is glutamic acid or lysine;
$Xaa_m$ is threonine or alanine;
$Xaa_n$ is methionine;
$Xaa_o$ is arginine;
$Xaa_p$ is lysine or threonine;
$Xaa_1$ is proline;
$Xaa_2$ is arginine;
$Xaa_3$ is cysteine;
$Xaa_4$ is glycine;
$Xaa_5$ is valine or asparagine;
$Xaa_6$ is proline;
$Xaa_7$ is aspartic acid;
$Xaa_8$ is valine or leucine;
$Xaa_9$ is alanine or glycine;
$Xaa_{10}$ is asparagine or arginine;
$Xaa_{11}$ is tyrosine or phenylalanine;
$Xaa_{12}$ is asparagine or glutamine;
$Xaa_{13}$ is phenylalanine or threonine;
$Xaa_{14}$ is phenylalanine;
$Xaa_{15}$ is proline or glutamic acid;
$Xaa_{16}$ is arginine or glycine;
$Xaa_{17}$ is lysine or aspartic acid;
$Xaa_{18}$ is proline or leucine;
$Xaa_{19}$ is lysine The invention also contemplates modifying the polypeptides to, for example, stabilize them, to facilitate their uptake and absorption and/or to improve any other characteristic or property of the polypeptides that is known to one of skill in art. For example, the polypeptides may be cyclized, charges on the polypeptides may be neutralized, and/or the polypeptides may be linked to other chemical moieties.

Polypeptides may be cyclized by any method available to one of skill in the art. For example, the N-terminal and C-terminal ends may be condensed to form a polypeptide bond by known procedures. Functional groups present on the side chains of amino acids in the polypeptides may also be joined to cyclize the polypeptides of the invention. For example, functional groups that may form covalent bonds include —COOH and —OH; —COOH and —NH$_2$; and —COOH and —SH. Pairs of amino acids that may be used to cyclize a polypeptide include, Asp and Lys; Glu and Lys; Asp and Arg; Glu and Arg; Asp and Ser; Glu and Ser; Asp and Thr; Glu and Thr; Asp and Cys; and Glu and Cys. Other examples of amino acid residues that are capable of forming covalent linkages with one another include cysteine-like amino acids such Cys, hCys, β-methyl-Cys and Pen, which may form disulfide bridges with one another. Examples of cysteine-like amino acid residues include Cys and Pen. Other pairs of amino acids that may be used for cyclization of the polypeptide will be apparent to those skilled in the art.

The groups used to cyclize a polypeptide need not be amino acids. Examples of functional groups capable of forming a covalent linkage with the amino terminus of a polypeptide include carboxylic acids and esters. Examples of functional groups capable of forming a covalent linkage with the carboxyl terminus of a polypeptide include —OH, —SH, —NH$_2$ and —NHR where R is $(C_1-C_6)$ alkyl, $(C_1-C_6)$ alkenyl or $(C_1-C_6)$ alkynyl.

The variety of reactions between two side chains with functional groups suitable for forming such inter-linkages, as well as reaction conditions suitable for forming such inter-linkages, will be apparent to those of skill in the art. Reaction conditions used to cyclize the polypeptides are generally sufficiently mild so as not to degrade or otherwise damage the polypeptide. Suitable groups for protecting the various functionalities as necessary are well known in the art (see, e.g., Greene & Wuts, 1991, 2nd ed., John Wiley & Sons, NY), as are various reaction schemes for preparing such protected molecules.

In one embodiment the charges at the N-terminal and C-terminal ends may be effectively removed. This may be done by any method available to one of skill in the art, for example, by acetylating the N-terminus and amidating the C-terminus.

Methods for preparing cyclic polypeptides and modifying polypeptide in other ways are well-known in the art (see, e.g., Spatola, 1983, Vega Data 1(3) for a general review); Spatola, 1983, "Peptide Backbone Modifications" In: Chemistry and Biochemistry of Amino Acids polypeptides and Proteins (Weinstein, ed.), Marcel Dekker, New York, p. 267 (general review); Morley, 1980, Trends Pharm. Sci. 1:463-468; Hudson et al., 1979, Int. J. Prot. Res. 14:177-185 (—CH$_2$NH—, —CH$_2$CH$_2$—); Spatola et al., 1986, Life Sci. 38:1243-1249 (—CH$_2$—S); Hann, 1982, J. Chem. Soc. Perkin Trans. I. 1:307-314 (—CH═CH—, cis and trans); Almquist et al., 1980, J. Med. Chem. 23:1392-1398 (—COCH$_2$—); Jennings-White et al., Tetrahedron. Lett. 23:2533 (—COCH$_2$—); European Patent Application EP 45665 (1982) CA:97:39405 (—CH(OH)CH$_2$—); Holladay et al., 1983, Tetrahedron Left. 24:4401-4404 (—C(OH)CH$_2$—); and Hruby, 1982, Life Sci. 31:189-199 (—CH$_2$—S—).

When present in a composition, the amount of polypeptides of the invention may generally be in a range from about 0.001% to about 90% by weight of the composition. For example, the polypeptides may form from about 0.5% to about 60% by weight of the composition. In another embodiment, the polypeptides may form from about 1.0% to about 50% by weight of the composition.

In another embodiment, the inhibitory compounds of the invention may be natural, plant based compounds capable of inhibiting CRP/Fn complexation as herein described. For example, in one embodiment, the compounds of the invention may include gibberellic acid compounds and jasmonic acid compounds.

Gibberellic acid compounds comprise a class of compounds that is 10 also referred to as gibberellins. Gibberellins are plant hormones that affect a wide variety of processes throughout the life cycle of plants, including seed germination, stem elongation, flower induction, anther development, and seed and pericarp growth. Gibberellins are tetracyclic diterpenoid acids found in fungi and higher plants having the ent-gibberellane ring system shown in the following structure (IV):

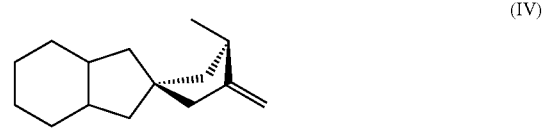

Two main types of gibberellins exist, the first includes $C_{20}$-gibberellins, which have a general 20 carbon backbone structure as shown below in structure (V):

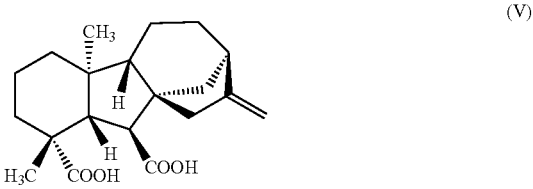

The second main type is $C_{19}$-gibberellins, in which the twentieth carbon atom has been lost due to metabolism. The carboxylic acid at carbon-19 bonds to carbon-10 to produce a lactone bridge in almost all of the $C_{19}$-gibberellins. The general backbone structure for $C_{19}$-gibberellins is structure (VI):

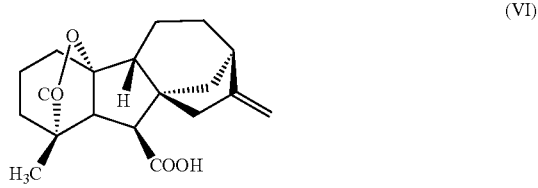

The ent-gibberellane ring system may contain many structural modifications, accounting for the large number of known gibberellins. Naturally occurring gibberellins with identified structures are allocated an "A number" (MacMillan et al. Nature 217:170-171(1968)). At present, 126 naturally occurring gibberellins of plant and fungal origin are known. Current structural information on gibberellins is generally known to those of ordinary skill in the art and thus details have not been described herein.

Compounds of the present invention include gibberellins such as those specifically shown above as well as variations of these structures. Variations in gibberellin structure may arise in several ways. For example, carbon-20 may exist in different oxidative states, e.g., methyl, hydroxymethyl, aldehyde, or carboxylic acid. The ent-gibberellane skeleton, especially that of the $C_{19}$-gibberellins, may also contain additional functional groups. Hydroxyl groups are frequently inserted into the ring system, however, insertion of epoxide and ketone functions also occurs, although less commonly.

Gibberellins of the invention may optionally exist as conjugates, for example with a molecule of glucose, e.g., by an ether or an ester linkage.

In one embodiment, the gibberellic acid compound may be gibberellic acid, which has the following structure (VII)

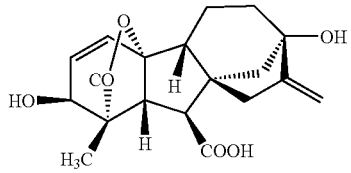

(VII)

In one embodiment, the inhibitory compounds of the present invention include jasmonic acid compounds. Jasmonic acid compounds employed in the invention may include any jasmonic acid and jasmonic acid derivatives as are generally known to one of skill in the art. Such compounds include, for example, jasmonic acid, methyl jasmonate and isomers thereof as well as synthetic and natural stereoisomers of jasmonic acid, dihydrojasmonic acid, hydroxy jasmonic acid and dihydro-hydroxy jasmonic acid. Further examples of jasmonic acid derivatives that may inhibit complexation of CRP with Fn include compounds having the general structure (VII):

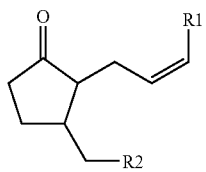

(VIII)

wherein:
R1 is alkyl;
R2 is COO(R3), or —(CH$_2$)$_n$—OX, where
  n is an integer of from 1 to 20;
  R3 is H or alkyl and
  X is H or 1 to 6 sugar residues (e.g., hexose or pentose).

In general, the alkyl groups employed in such jasmonic acid compounds have about one to twenty carbon atoms, although in some embodiments smaller alkyl groups are used, for example, alkyl groups with about one to eight carbon atoms. Alkyl groups with even lower numbers of carbon atoms may also be used, for example, alkyl groups with one to six, or one to three carbon atoms.

In one embodiment, jasmonic acid may be utilized. Jasmonic acid is a compound of formula VII wherein R1 is C$_2$H$_5$ and R2 is COOH.

Another jasmonic acid compound encompassed by the invention is a compound of the following structure (IX):

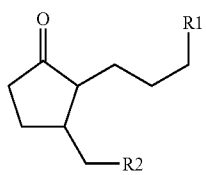

(IX)

wherein:
R1 is alkyl;
R2 is COO(R3), or —(CH$_2$)$_n$—OX, where n is an integer of from 1 to 20;
R3 is H or alkyl; and
X is H or 1 to 6 sugar residues (e.g., hexoses or pentoses).

In some embodiments, dihydrojasmonic acid may be employed in the compositions of the invention. Dihydrojasmonic acid is a compound of the above formula (IX) wherein R1 is C$_2$H$_5$ and R2 is COOH.

Another jasmonic acid compound employed in the invention is a compound of formula (X)

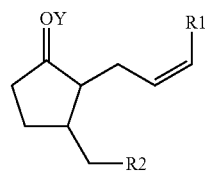

(X)

wherein:
R1 is alkyl;
R2 is COO(R3), or —(CH$_2$)$_n$—OX, where
  n is an integer of from 1 to 20;
  R3 is H or alkyl;
  X is H or 1 to 6 sugar residues (e.g., hexoses or pentoses); and
  Y is H, alkyl, or 1 to 6 sugar residues (e.g., hexoses or pentoses).

In some embodiments, hydroxyjasmonic acid is employed in the compositions of the invention. Hydroxyjasmonic acid is a compound of formula (X) wherein R1 is C$_2$H$_5$ and R2 is COOH.

Another jasmonic acid compound employed in the invention is a compound of formula (XI)

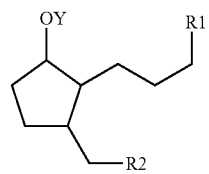

(XI)

wherein:
R1 is alkyl;
R2 is COO(R3), or —(CH$_2$)$_n$—OX, where
  n is an integer of from 1 to 20;
  R3 is H or alkyl;
  X is H or 1 to 6 sugar residues (e.g., hexoses or pentoses); and
  Y is H, alkyl, or 1 to 6 sugar residues (e.g., hexoses or pentoses).

In some embodiments, dihydro-hydroxyjasmonic acid is employed in the compositions of the invention. Dihydro-hydroxyjasmonic acid is a compound of formula (XI) wherein R1 is C$_2$H$_5$ and R2 is COOH.

When present in the compositions of the present invention, gibberellic acids and jasmonic acids as herein disclosed may be present in an amount from about 0.001% to about 90%, from about 0.001% to about 50%, or from about 0.01% to about 20%, or from about 0.01% to about 10%, or from about 0.05% to about 5%, or from about 0.05% to about 2% by weight of the composition. According to one embodiment of the invention, composition including the disclosed compounds may include an amount of an active gibberellic acid compound and/or a jasmonic acid compound ranging from about $10^{-4}$ M to about $10^{-6}$ M.

The inhibitory compounds of the present invention encompass other natural and synthetic compounds that may be identified according to the screening methods as herein described, in addition to those specifically described above. In particular, the compounds specifically described above are exemplary inhibitory compounds that have been identified according to the disclosed screening methods and are not intended to be limiting in any way in regard to the inhibitory compounds encompassed by the present invention.

Applications

According to the present invention, the disclosed inhibitory compounds and compositions comprising the disclosed compounds may be utilized to inhibit the complexation of CRP with Fn.

For example, compositions including the polypeptides, the natural plant compounds, or any other inhibitory compound that may be identified according to the methods described herein may be formulated and used in a manner that improves the healing process through inhibition of the formation of a C-reactive protein/fibronectin complex. In one embodiment, the disclosed compositions may be beneficial in treatment of tissue damage at which CRP/Fn complex may form, e.g., wound or trauma sites. In one particular embodiment, the disclosed compositions may be beneficial in treatment of chronic wounds.

In one embodiment, the disclosed compounds and compositions comprising the compounds may be utilized to inhibit formation of CRP/Fn complex at conditions typical of disease states in which CRP/Fn complex may form, for instance at low pH conditions. For example, the disclosed compounds may be beneficial in treatment of people or animals afflicted with disease such as cardiovascular disease, inflammatory disease (e.g., rheumatoid arthritis, juvenile chronic arthritis, ankylosing spondylitis, psoriatic arthritis, systemic vasculities, polymyalgia rheumatica, Reiter's disease, and Crohn's disease), infection, obesity, transplant rejection (e.g., allograft rejection such as is found in renal transplantation), necrosis due to e.g., myocardial infarction, diabetes, renal disease, tumor embolisation or acute pancreatitis, or trauma due to wounds, burn, or fractures.

The disclosed compounds are not limited to either in vivo use or use at low pH, however. In particular, the disclosed compounds may be utilized to inhibit complexation of CRP with Fn independent of pH in vivo as well as ex vivo. For example, as CRP is a very sensitive index of ongoing inflammation, it may provide a valuable adjunct to a careful clinical assessment. In order to take advantage of the sensitivity of CRP levels in determining an overall state of health, accurate determination of CRP levels is required. Accordingly, reaction of CRP with other sample components prior to or during an assay procedure is to be avoided, in particular as such reaction could detrimentally effect the accurate assessment of CRP level in the sample. As such, one embodiment the disclosed compounds is directed to utilization of the compounds in conjunction with CRP assay procedures as are generally known to one of skill in the art so as to inhibit complexation of CRP with Fn and thus provide a more accurate determination of the CRP levels in the sample. Of course, the disclosed compounds would be equally effective in providing a method for a more accurate determination of Fn levels in a sample.

In other embodiments of the invention, the disclosed compounds may be utilized in examination of the properties of various active agents during disease states. For example, the disclosed compounds may be beneficially utilized to further examine the roles of MMPs, CRP, Fn, proinflammatory mediators, or any other biomolecules that interact with CRP, Fn or MMPs during formation of or recovery from disease. Through utilization of the disclosed compounds, for instance in animal model studies, broader understanding of agents demonstrating abnormal activity during disease or upon tissue damage may be realized. For instance, increased understanding of the wound healing properties of acute phase reactants may be realized.

The effective amount of a compound of the present invention may obviously vary with the route of administration as well as with the particular application of the compounds. For example, when considering a therapeutic composition, an amount between 30 to 112,000 μg per kg of body weight may be effective for intravenous administration. However, the particular amount of the disclosed compounds required for a specific application may vary not only with the route of administration, but also the nature of the condition being treated and the age and condition of the patient and will be ultimately at the discretion of the attendant physician or clinician.

The dosage and method of administration may vary depending upon the location of the skin or tissue to be treated and/or upon the size of the disease site or the severity of the wound. Useful dosages of the compounds may be determined by correlating their in vitro activity and in vivo activity in animal models as is generally known in the art. The compounds may conveniently be administered in unit dosage form; for example, containing about 0.001 μg to about 10 mg, conveniently about 0.01 μg to about 5 mg, more conveniently, about 0.10 μg to about 1 mg, and even more conveniently about 1.0 μg to 500 μg of material per unit dosage form. The desired dose may be presented in a single dose, as divided doses, or as a continuous infusion. The desired dose may also be administered at appropriate intervals, for example, as two, three, four or more sub-doses per day. One of skill in the art may readily prepare and administer an effective formulation from available information using the teachings provided herein.

The compounds of the invention may be formulated as pharmaceutical compositions and administered to a mammalian host, such as a human patient, in a variety of dosage forms adapted to the chosen route of administration, i.e., orally or parenterally, by intravenous, intramuscular, topical or subcutaneous routes.

Thus, the compounds may be systemically administered, for example, intravenously or intraperitoneally by infusion or injection. The compounds may also be locally administered, for example, by infusion or injection into a localized area, or by implantation of a drug delivery device into an affected area. Solutions of the compounds may be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion or topical application may include sterile aqueous solutions or dispersions or sterile powders comprising the active ingredient that are adapted for the extemporaneous preparation of sterile injectable or infusible solutions or dispersions, optionally encapsulated in liposomes. In any case, the ultimate dosage form must be sterile, fluid and stable under the conditions of manufacture and storage. The liquid carrier or vehicle may be a solvent or liquid dispersion medium comprising, for example, water, ethanol, a polyol (for example, glycerol, propylene glycol, liquid polyethylene glycols, and so forth), vegetable oils, nontoxic glyceryl esters, and suitable mixtures thereof. The proper fluidity may be maintained, for example, by the formation of liposomes, by the maintenance of the required particle size in the case of dispersions or by the use of surfactants. The prevention of the action of microorganisms may be brought about by various antibacterial and antifungal agents, for example, parabens, chlorobutanol, phenol, sorbic acid, thimerosal, and so forth. In some cases, one of skill in the art may choose to include isotonic agents, for example, sugars, buffers or sodium chloride. Prolonged absorption of the injectable compositions may be brought about by the use in the compositions of agents delaying absorption, for example, aluminum monostearate and gelatin.

Sterile injectable solutions may be prepared by incorporating the disclosed compounds in the required amount in the appropriate solvent with various of the other ingredients enumerated above, as required, followed by filter sterilization. In the case of sterile powders for the preparation of sterile injectable solutions, methods of preparation include, for example, vacuum drying and the freeze-drying techniques, which yield a powder of the active ingredient plus any additional desired ingredient present in the previously sterile-filtered solutions.

In some instances, the disclosed compounds may be administered orally, in combination with a pharmaceutically acceptable vehicle such as an inert diluent or an assimilable edible carrier. They may be enclosed in hard or soft shell gelatin capsules, may be compressed into tablets, or may be incorporated directly with food. For oral therapeutic administration, the compounds may be combined with one or more excipients and used in the form of ingestible tablets, buccal tablets, troches, capsules, elixirs, suspensions, syrups, wafers, and so forth. Such compositions and preparations should generally contain at least 0.1% of active compound. The percentage of the compositions and preparations may, of course, be varied and may conveniently be between about 2% to about 90% of the weight of a given unit dosage form. The amount of active compound in such therapeutically useful compositions is such that an effective dosage level will be obtained.

Tablets, troches, pills, capsules, and so forth including the disclosed compounds may also contain the following: binders such as gum tragacanth, acacia, corn starch or gelatin; excipients such as dicalcium phosphate; a disintegrating agent such as corn starch, potato starch, alginic acid and so forth; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and so forth. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially nontoxic in the amounts employed. In addition, the disclosed compounds may be incorporated into sustained-release preparations and devices.

Useful solid carriers include finely divided solids such as talc, clay, microcrystalline cellulose, silica, alumina and so forth. Useful liquid carriers include water, alcohols or glycols or water-alcohol/glycol blends, in which the present compounds may be dissolved or dispersed at effective levels, optionally with the aid of non-toxic surfactants. Adjuvants such as fragrances and additional antimicrobial agents may be added to optimize the properties for a given use.

Thickeners such as synthetic polymers, fatty acids, fatty acid salts and esters, fatty alcohols, modified celluloses or modified mineral materials may also be employed with liquid carriers to form spreadable pastes, gels, ointments, soaps, and so forth, for application directly to the skin of the user.

In one embodiment, the compounds of the invention may be administered topically, such as for wound treatment. The disclosed compounds may be administered topically by any means either directly or indirectly to the selected tissue as sprays, foams, powders, creams, jellies, pastes, suppositories or solutions. The term paste is intended to include creams and other viscous spreadable compositions such as are often applied directly to the skin or spread onto a bandage or dressing. Compounds of the invention may be covalently attached, adsorbed or otherwise applied to a skin covering or wound dressing material. To facilitate healing after surgery, the disclosed compounds may be applied directly to target tissues or to implantable prosthetic devices. The compositions may be administered by aerosol, as foam or as a mist along with other agents directly onto the skin or wound.

The compounds may be administered in a formulation that may include an emulsion of the polypeptide in a wax, oil, an emulsifier, water, and/or a substantially water-insoluble material that forms a gel in the presence of water. The formulation provides the desirable properties of an emulsion, in that it is spreadable and has the creamy consistency of an emulsion, yet that does not break down when subjected to normal sterilization procedures, e.g. steam sterilization, because the gel stabilizes the emulsion. It also exhibits better water retention properties than a conventional gel because water is held both in the emulsion and in the gel.

The formulation may also contain a humectant to reduce the partial vapor pressure of the water in the cream or lotion to reduce the rate at which the cream or lotion dries out. Suitable humectants are miscible with water to a large extent and are generally suitable for application to the skin. Polyols are suitable for the purpose. Examples of suitable polyols may include monopropylene glycol or glycerine (glycerol). The polyol may be present in proportions of about 20-50% (by weight) of the total formulation; alternatively the range may be, for example, about 30-40%. This relatively high proportion of polyol also ensures that if the paste should dry out to any degree, the resulting paste remains soft and flexible because the glycerine may act as a plasticiser for the polymer. When the paste is applied on a bandage, for example, it may therefore still be removed easily from the skin when the paste has lost water without the need to cut the bandage off. The polyol also has the advantage of functioning to prevent the proliferation of bacteria in the paste when it is in contact with the skin or wound, particularly infected wounds.

A formulation of the invention may include other ingredients. Ingredients that may be used include: zinc oxide, ichthammol, calamine, silver suphadiazine, chlorhexidine acetate, coal tar, chlorhexidine gluconate, salicylic acid, metronidazole or other antibacterial agents, or a combination thereof. Other ingredients may also be found suitable for incorporation into a cream. In one embodiment, the additional components should be suitable for application to keratinous tissue, for instance when the composition is to be in contact with human keratinous tissue.

Other ingredients may be included in topical formulations in beneficial amounts, for example, up to about 15 wt % of zinc oxide may be added; typically 6-10% of zinc oxide is used, possibly in combination with another ingredient such as ichthammol (0-3 wt %) and/or calamine (0-15 % wt). Ichthammol or calamine may also be used alone. Chlorhexidine acetate may be used at a concentration of up to 1% by weight; 0.5 wt % is typical.

The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents (clove oil, menthol, camphor, eucalyptus oil, eugenol, menthyl lactate, witch hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, opacifying agents, pH adjusters, propellants; reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and panthenol derivatives), aloe vera, pantothenic acid, pantothenic acid derivatives, allantoin, bisabolol, and dipotassium glycyrrhizinate, skin treating agents, thickeners, and vitamins and derivatives thereof.

The compositions of the present invention may comprise a skin soothing or skin-healing compound. Skin soothing or skin healing compounds suitable for use herein include panthenoic acid derivatives (including panthenol, dexpanthenol, and ethyl panthenol), aloe vera, allantoin, bisabolol, and dipotassium glycyrrhizinate. A safe and effective amount of a skin soothing or skin healing compound may be added to the present composition, foe example, from about 0.1% to about 30%, or from about 0.5% to about 20%, or from about 0.5% to about 10%, by weight of the composition formed.

The compositions of the present invention may contain an anti-microbial or anti-fungal compound. Such compounds are capable of destroying microbes, preventing the development of microbes or preventing the pathogenic action of microbes. A safe and effective amount of an anti-microbial or anti-fungal compound may be added to the present compositions, for example, from about 0.001% to about 10%, or from about 0.01% to about 5%, or from about 0.05% to about 2%.

Examples of antimicrobial and antifungal compounds include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Examples of compounds useful herein include those selected from benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof.

One example of a wax for emulsion of the disclosed compounds is glyceryl monostearate, or a combination of glyceryl monostearate and PEG 100 stearate that is available commercially as CITHROL GMS/AS/NA from Croda Universal Ltd. This combination provides both a wax and an emulsifier (PEG 100 stearate) that is especially compatible with the wax, for forming an emulsion in water. A second emulsifier may be included in the formulation to increase the stability of the emulsion, for example, a PEG20 stearate, such as CITHROL 1 OMS that is supplied by Croda Universal Ltd. The total concentration of emulsifier in the cream should normally be in the range of from 3-15%. Where two emulsifiers are used, one may be present in a greater concentration than the other.

The disclosed compounds and compositions including the disclosed compounds may be packaged into tubes, tubs or other suitable forms of container for storage or may be spread onto a substrate and then subsequently packaged. Suitable substrates include dressings, including film dressings, and bandages.

The presently disclosed invention may be better understood by reference to the following example.

EXAMPLE

An in vitro model was designed to determine inhibitory effect of several different test compounds on CRP/Fn binding.

Surface plasmon resonance (SPR) measurements were performed using a Biacore® X system and amine coupling kit for immobilization. SPR response was measured in resonance units (RU), and was indicative of SPR angle change, where 1000RU correspond to an angle change of ~0.1°. All experiments were performed at 25° C., unless otherwise specified.

The SPR technology used is based on optical phenomena in which the measured response depends on a change in refractive index in the close vicinity of the sensor chip surface. The response in such systems is proportional to the mass of analyte bound to the surface. The SPR method was used to monitor continuous analysis over the course of the interaction.

Figure 2:
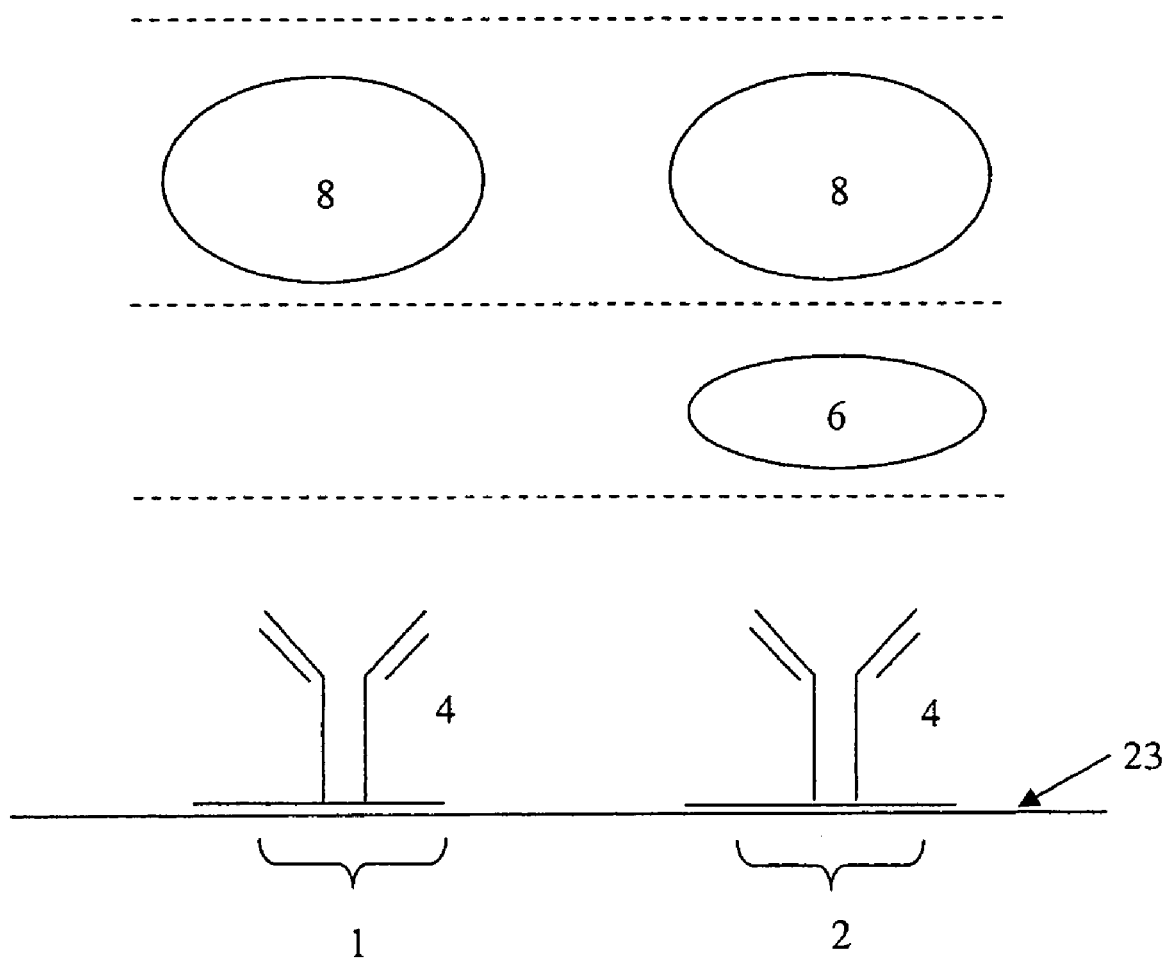
FIG. 2 depicts an exemplary screening process of the present invention.

During the process, and as illustrated in FIG. 2, a known CRP antibody 4 available from BiosPacific, Emeryville, Calif. (catalog number A58110228P), which specifically binds to calcium/phosphocholine site of CRP, was immobilized on a surface of a sensor chip 23 (CM5, carboxyl functionalized) via amine coupling chemistry as is generally known in the art.

Following immobilization of the antibody to the surface of the chip 23, 10 μL of CRP antigen 6 (50 μg/mL) was injected in flow channel 2. Following this injection, 60 μL of an Fn solution 8 was injected into both flow channel 1 and flow channel 2 for two minutes duration (association phase), followed by 2 minutes delay time (dissociation phase). The SPR response was then measured, and the sensor chip surface (both channels) was generated with 10 μL of 10 mM HCl.

The process was repeated with an Fn solution including no inhibitor material as a control as well as several Fn solutions including various inhibitor compounds as herein described. Fn concentration was 1 mg/mL in all solutions. Results are shown below in Table 3. Percent inhibition values were derived by subtracting the control response units from the value obtained for a test sample, dividing the result by the control response units, and multiplying by 100.

TABLE 3

| Inhibitor | Concentration of Inhibitor (μM) | SPR Response (RU) | % Inhibition |
|---|---|---|---|
| Control | — | 118 | (control) |
| 19-mer (SEQ ID NO.: 11) | 50 | 76 | 35.6 |
| 10-mer (SEQ ID NO.: 12) | 50 | 76 | 35.6 |
| 9-mer (SEQ ID NO.: 16) | 50 | 119 | 0.0 |
| Gibberellic acid | 200 | 90 | 23.7 |
| Jasmonic acid | 40 | 94 | 20.4 |

As may be seen with reference to Table 3, the binding affinities of Fn to CRP were obtained, and the effect of several exemplary compounds as herein described was also obtained. Among the screened compounds, the 19-mer (SEQ ID NO.: 11), showed significant inhibitory effect on CRP/Fn binding, with the 10-mer (SEQ ID NO.:12), gibberellic acid, and jasmonic acid, showing somewhat less inhibitory effect at these conditions. The 9-mer (SEQ ID NO.:16) showed no significant effect on CRP/Fn binding.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention which is defined in the following claims and all equivalents thereto. Further, it is identified that many embodiments may be conceived that do not achieve all of the advantages of some embodiments, yet the absence of a particular advantage shall not be construed to necessarily mean that such an embodiment is outside the scope of the present invention.

What is claimed is:

1. A method for identifying a gibberellic acid or a jasmonic acid compound that inhibits the complexation of C-reactive protein with fibronectin, the method comprising:

contacting a first polypeptide with a second polypeptide in the presence of a gibberellic acid or jasmonic acid test compound to form a complex of the first polypeptide with the second polypeptide, the first polypeptide comprising at least a segment of a C-reactive protein, the first polypeptide including the fibronectin binding site of the C-reactive protein and the second polypeptide comprising at least a segment of a fibronectin protein, the second polypeptide including the C-reactive binding site of the fibronectin; and determining whether complexation of the first polypeptide with the second polypeptide is decreased in the presence of said gibberellic acid or jasmonic acid test compound as compared to a control containing no gibberellic acid or jasmonic acid compound, wherein the first polypeptide and the second polypeptide form a complex in the absence of gibberellic acid or jasmonic acid compound and a decrease in said complexation is an indication that said gibberellic acid or jasmonic acid compound inhibits the complexation of C-reactive protein to fibronectin.

2. The method of claim 1, wherein either the first polypeptide or the second polypeptide is immobilized in a detection zone of a separation device.

3. The method of claim 2, wherein the step of determining whether complexation of the first polypeptide with the second polypeptide is decreased in the presence of the gibberellic acid or jasmonic acid compound includes generating a detection signal within the detection zone, the detection signal corresponding to the complexation of the first polypeptide with the second polypeptide.

4. The method of claim 2, wherein the detection zone is in fluid communication with detection probes for generating the detection signal.

5. The method of claim 4, wherein the detection probes are conjugated with the first polypeptide.

6. The method of claim 4, wherein the detection probes are conjugated with the second polypeptide.

7. The method of claim 1, wherein the first polypeptide comprises SEQ ID NO.: 20.

8. The method of claim 1, wherein the first polypeptide comprises SEQ ID NO.: 19.

9. The method of claim 1, wherein the second polypeptide comprises SEQ ID NO.: 18.

10. The method of claim 1, wherein the second polypeptide comprises SEQ ID NO.: 17.

11. The method of claim 2, the separation device comprising a fluidic medium, the method further comprising applying a test sample including the gibberellic acid or jasmonic acid compound to the fluidic medium at an application site, the gibberellic acid or a jasmonic acid compound flowing through the fluidic medium from the application site to the detection zone within which the first polypeptide contacts the second polypeptide in the presence of the gibberellic acid or jasmonic acid test compound.

12. The method of claim 11, the separation device further comprising a conjugate pad located upstream of the detection zone, the conjugate pad carrying detection probes in dehydrated form that are free to migrate upon rehydration with the test sample.

13. The method of claim 12, wherein the detection probes are modified with either the first polypeptide or the second polypeptide to form conjugated detection probes.

14. The method of claim 11, the separation device further comprising an absorbent pad located downstream from the detection zone, the method further comprising the test sample flowing from the application zone to the detection zone and then to the absorbent pad.

15. The method of claim 11, the method further comprising combining the test sample with either the first polypeptide or the second polypeptide upstream of the detection zone.

16. The method of claim 15, wherein the first polypeptide or the second polypeptide that is combined with the test sample upstream of the detection zone is modified with detection probes to form conjugated detection probes.

17. The method of claim 15, wherein the first polypeptide or the second polypeptide that is combined with the test sample upstream of the detection zone is combined with the test sample prior to application of the test sample to the fluidic medium.

* * * * *

UNITED STATES PATENT AND TRADEMARK OFFICE
CERTIFICATE OF CORRECTION

| | | |
|---|---|---|
| PATENT NO. | : 7,645,583 B2 | Page 1 of 1 |
| APPLICATION NO. | : 11/302994 | |
| DATED | : January 12, 2010 | |
| INVENTOR(S) | : Boga et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 908 days.

Signed and Sealed this

Sixteenth Day of November, 2010

David J. Kappos
*Director of the United States Patent and Trademark Office*